United States Patent
Stiles et al.

(10) Patent No.: US 7,655,775 B2
(45) Date of Patent: Feb. 2, 2010

(54) EXPRESSION VECTORS FOR TREATING BACTERIAL INFECTIONS

(75) Inventors: Michael E. Stiles, Edmonton (CA); Liru Wang, Edmonton (CA); Marius Jacobus van Belkum, Edmonton (CA)

(73) Assignee: CanBiocin, Inc., Edmonton, Alberta (CA)

( * ) Notice: Subject to any disclaimer, the term of this patent is extended or adjusted under 35 U.S.C. 154(b) by 471 days.

(21) Appl. No.: 11/010,569

(22) Filed: Dec. 14, 2004

(65) Prior Publication Data

US 2006/0018879 A1 Jan. 26, 2006

Related U.S. Application Data

(63) Continuation-in-part of application No. 09/883,343, filed on Jun. 19, 2001, now abandoned, which is a continuation-in-part of application No. 08/924,629, filed on Sep. 5, 1997, now Pat. No. 6,403,082, application No. 11/010,569, which is a continuation-in-part of application No. 10/916,641, filed on Aug. 12, 2004, now abandoned.

(51) Int. Cl.
*C07H 21/02* (2006.01)
*A61K 38/00* (2006.01)
*C12N 15/00* (2006.01)
*C12N 15/74* (2006.01)
*C12P 21/04* (2006.01)

(52) U.S. Cl. .................. 536/23.1; 530/300; 435/471; 435/440; 435/71.1; 435/70.1

(58) Field of Classification Search .............. 435/70.1, 435/71.1, 440, 471; 536/23.1; 530/300, 530/825

See application file for complete search history.

(56) References Cited

U.S. PATENT DOCUMENTS

| | | | |
|---|---|---|---|
| 6,403,082 B1 * | 6/2002 | Stiles et al. | 424/93.2 |
| 2003/0039632 A1 * | 2/2003 | Stiles et al. | 424/93.2 |
| 2006/0037087 A1 * | 2/2006 | van Belkum et al. | 800/10 |

OTHER PUBLICATIONS

Gilson, L. et al., "Genetic analysis of an MDR-like export system: the secretion of colicin V." EMBO Journal, 1999, pp. 3875-3884, vol. 9, No. 12.

Horn, N. et al, "Nisin-contolled production of pediocin PA-1 and colicin V in nisin-and non-nisin-producing Lactococcus lactis strains", Applied and Environmental Microbiology, Aug. 2004, pp. 5030-5032, vol. 70, No. 8.

McCormick, J.K. et al., "Colicin V can be produced by lactic acid bacteria." Letters in Applied Microbiology, 1991, pp. 37-41, vol. 29.

Pinou, T. et al., "Nucleotide polymorphism in microcin V plasmids", Plasmid, 2001, pp. 1-9, vol. 46.

Riley, M.A. et al., "Bacteriocins: evolution, ecology, and application", Annual Review of Microbiology, 2002, pp. 117-137, vol. 56, Dec. 1, 2008.

Stahl, C.H. et al., "Inhibitory Activities of colicin against *Escherichia coli* strains responsible for postweaning diarrhea and edema disease in swine", Antimicrobial Agents and Chemotherapy, Aug. 2004, pp. 3119-3121, vol. 48, No. 8.

* cited by examiner

*Primary Examiner*—Robert B Mondesi
*Assistant Examiner*—Lakia J Tongue
(74) *Attorney, Agent, or Firm*—William J. Bundren

(57) ABSTRACT

The present invention is compositions and methods for producing anti-bacterial polypeptides, and for using those compositions and methods for treating diseases and conditions caused by a bacterial infection. More specifically, the compositions and methods include treating a gram-negative bacterium with a gram-positive host that produces a polypeptide effective against the gram-negative bacterium.

4 Claims, 16 Drawing Sheets

Figure 1: Schematic representation of plasmid pCaT.

Figure 5A. Nucleotide sequence of native colicin V SEQ. I.D. NO. 25
gcttcagggcgtgatattgcgatggctataggaacactatccgggcaatttgttgcag
gaggaattggagcagctgctgggggtgtggctggaggtgcaatatatgactatgcatc
cactcacaaacctaatcctgcaatgtctccatccggtttagggggaacaattaagcaa
aaacccgaagggatacct tcagaagcatggaactatgctgcgggaagattgtgtaatt
ggagtccaaataatcttagtgatgtttgttta Figure 5B. Nucleotide sequence of colicin VM SEQ. I.D. NO. 3
gcttcagggcgtgatattgcgatggctataggaacactatccgggcaatttgttgcag
gaggaattggagcagctgctgggggtgtggctggaggtgtggctggaggtgcaatata
tgactatgcatccactcacaaacctaatcctgcaatgtctccatccggtttaggggga
acaattaagcaaaaacccgaagggatacct tcagaagcatggaactatgctgcgggaa
gattgtgtaattggagtccaaataatcttagtgatgtttgttta Figure 5C. Native amino acid sequence of colicin V SEQ. I.D. NO. 26
ASGRDIAMAIGTLSGQFVAGGIGAAAGGVAGGAIYDYA
STHKPNPAMSPSGLGGTIKQKPEGIPSEAWNYAAGRLC
NWSPNNLSDVCL Figure 5D. Amino acid sequence of colicin VM SEQ. I.D. NO. 4
ASGRDIAMAIGTLSGQFVAGGIGAAAGGVAGGVAGGA
IYDYASTHKPNPAMSPSGLGGTIKQKPEGIPSEAWNYA
AGRLCNWSPNNLSDVCL

Figure 5

```
GATCCACCAAATGTCCATTTTTTAAATCACCTCTTTCATTAAATCTCA
TTAGTTAGTGTACCATATTTGACCGTCTAAAAGTATTTTGTAAAATAA
ATTTAATATTTAAATGAACAAAACTTAAGAGTTTTAAATGTAGGAAAA
TAGTTTAAATTCCTTGTAAAGTAAAAAACTTTACAAAGTATAAAAAA
AAGCTAGCAACTTTTGCAAAAAAATGATATGATATTCAAGTCCGAAGA
TAACAAAAATGTTTCTTCAAATATGGTTGAATGCTT
``` SEQ. I.D. NO. 5

SEQUENCE LISTING

<160> NUMBER OF SEQ ID NOS: 26

<210> SEQ ID NO 1
<211> LENGTH: 24
<212> TYPE: DNA
<213> ORGANISM: Unknown
<220> FEATURE:
<223> OTHER INFORMATION: mutant colicin gene fragment

<400> SEQUENCE: 1
gtggctggag gtgtggctgg aggt                                              24

<210> SEQ ID NO 2
<211> LENGTH: 8
<212> TYPE: PRT
<213> ORGANISM: Unknown
<220> FEATURE:
<223> OTHER INFORMATION: mutant colicin gene fragment

<400> SEQUENCE: 2

Val Ala Gly Gly Val Ala Gly Gly
1               5

<210> SEQ ID NO 3
<211> LENGTH: 276
<212> TYPE: DNA
<213> ORGANISM: Unknown
<220> FEATURE:
<223> OTHER INFORMATION: mutant colicin gene

<400> SEQUENCE: 3
gcttcagggc gtgatattgc gatggctata ggaacactat ccgggcaatt tgttgcagga      60
ggaattggag cagctgctgg gggtgtggct ggaggtgtgg ctggaggtgc aatatatgac     120
tatgcatcca ctcacaaacc taatcctgca atgtctccat ccggtttagg gggaacaatt     180
aagcaaaaac ccgaagggat accttcagaa gcatggaact atgctgcggg aagattgtgt     240
aattggagtc caaataatct tagtgatgtt tgttta                              276

<210> SEQ ID NO 4
<211> LENGTH: 92
<212> TYPE: PRT
<213> ORGANISM: Unknown
<220> FEATURE:
<223> OTHER INFORMATION: mutant colicin gene

<400> SEQUENCE: 4

Ala Ser Gly Arg Asp Ile Ala Met Ala Ile Gly Thr Leu Ser Gly Gln
1               5                   10                  15

Phe Val Ala Gly Gly Ile Gly Ala Ala Ala Gly Gly Val Ala Gly Gly
            20                  25                  30

Val Ala Gly Gly Ala Ile Tyr Asp Tyr Ala Ser Thr His Lys Pro Asn
        35                  40                  45

Pro Ala Met Ser Pro Ser Gly Leu Gly Gly Thr Ile Lys Gln Lys Pro
    50                  55                  60

Glu Gly Ile Pro Ser Glu Ala Trp Asn Tyr Ala Ala Gly Arg Leu Cys
65                  70                  75                  80

Asn Trp Ser Pro Asn Asn Leu Ser Asp Val Cys Leu
                85                  90

<210> SEQ ID NO 5
<211> LENGTH: 276
<212> TYPE: DNA
<213> ORGANISM: artificial sequence
<220> FEATURE:
<223> OTHER INFORMATION: p 15 promoter

<400> SEQUENCE: 5
gatccaccaa atgtccattt ttaaatcac ctctttcatt aaatctcatt agttagtgta       60
ccatatttga ccgtctaaaa gtattttgta aataaattt aatatttaaa tgaacaaaac     120
ttaagagttt taaatgtagg aaaatagttt aaattccttg taaagtaaaa aaactttaca    180

```
aagtataaaa aaaagctagc aacttttgca aaaaaatgat atgatattca agtccgaaga    240
taacaaaaat gtttcttcaa atatggttga atgctt                              276
```

<210> SEQ ID NO 6
<211> LENGTH: 28
<212> TYPE: DNA
<213> ORGANISM: artificial sequence
<220> FEATURE:
<223> OTHER INFORMATION: PCR primer
<220> FEATURE:
<221> NAME/KEY: misc_feature
<222> LOCATION: (4)..(9)
<223> OTHER INFORMATION: Sph I restriction site

<400> SEQUENCE: 6

```
cccgcatgct gaattcggtc ctcgggat                                        28
```

<210> SEQ ID NO 7
<211> LENGTH: 28
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (4)..(9)
<223> OTHER INFORMATION: SphI restriction site

<400> SEQUENCE: 7

```
cccgcatgcg gtaccactat ttataaac                                        28
```

<210> SEQ ID NO 8
<211> LENGTH: 28
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (5)..(10)
<223> OTHER INFORMATION: BcL I restriction site

<400> SEQUENCE: 8

```
tatatgatca ggtcctcggg atatgata                                        28
```

<210> SEQ ID NO 9
<211> LENGTH: 28
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (4)..(10)
<223> OTHER INFORMATION: Pst I restriction site

<400> SEQUENCE: 9

```
tatactgcag ggtaccgtct acagtctg                                        28
```

<210> SEQ ID NO 10
<211> LENGTH: 40
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (5)..(10)
<223> OTHER INFORMATION: Cla I restriction site

```
<400> SEQUENCE: 10
atatatcgat aggaagtatg atcaatggta aaaactatac                              40

<210> SEQ ID NO 11
<211> LENGTH: 35
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (5)..(10)
<223> OTHER INFORMATION: PstI restriction site

<400> SEQUENCE: 11
atatctgcag atatctagtt agagaatata atcca                                   35

<210> SEQ ID NO 12
<211> LENGTH: 12
<212> TYPE: DNA
<213> ORGANISM: Artificial Sequence
<220> FEATURE:
<223> OTHER INFORMATION: colicin V nucleotide sequence duplicate

<400> SEQUENCE: 12
gtggctggag gt                                                            12

<210> SEQ ID NO 13
<211> LENGTH: 8
<212> TYPE: PRT
<213> ORGANISM: Artificial Sequence
<220> FEATURE:
<223> OTHER INFORMATION: colicin V amino acid duplication

<400> SEQUENCE: 13

Val Ala Gly Gly Val Ala Gly Gly
1               5

<210> SEQ ID NO 14
<211> LENGTH: 40
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (5)..(10)
<223> OTHER INFORMATION: Cla I restriction site

<400> SEQUENCE: 14
atatatcgat aggaagtatg atcaatggta aaaactatac                              40

<210> SEQ ID NO 15
<211> LENGTH: 27
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (4)..(10)
<223> OTHER INFORMATION: Pst I restriction site

<400> SEQUENCE: 15
atatctgcag tctagttaga gaatata                                            27
```

```
<210> SEQ ID NO 16
<211> LENGTH: 41
<212> TYPE: DNA
<213> ORGANISM: Artificial Sequence
<220> FEATURE:
<223> OTHER INFORMATION: polylinker

<400> SEQUENCE: 16
gcatgcgaat tcgagctcgg tacccgggga tcctcctgca g        41

<210> SEQ ID NO 17
<211> LENGTH: 18
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(6)
<223> OTHER INFORMATION: Eco RI restriction site

<400> SEQUENCE: 17
gaattcgagc tcgcccgg                                  18

<210> SEQ ID NO 18
<211> LENGTH: 19
<212> TYPE: DNA
<213> ORGANISM: Artificial Sequence
<220> FEATURE:
<223> OTHER INFORMATION: PCR primer

<400> SEQUENCE: 18
ctgcaggtcg actctagag                                 19

<210> SEQ ID NO 19
<211> LENGTH: 18
<212> TYPE: DNA
<213> ORGANISM: Artificial Sequence
<220> FEATURE:
<223> OTHER INFORMATION: PCR primer

<400> SEQUENCE: 19
gaattcgagc tcgcccgg                                  18

<210> SEQ ID NO 20
<211> LENGTH: 34
<212> TYPE: DNA
<213> ORGANISM: Artificial Sequence
<220> FEATURE:
<223> OTHER INFORMATION: PCR primer

<400> SEQUENCE: 20
tgtgatacca agatgcattc aaccatattt gaag                34

<210> SEQ ID NO 21
<211> LENGTH: 33
<212> TYPE: DNA
<213> ORGANISM: Artificial Sequence
<220> FEATURE:
<223> OTHER INFORMATION: PCR primer

<400> SEQUENCE: 21
tatggttgaa tgcatcttgg tatcacaaac taa                 33

<210> SEQ ID NO 22
<211> LENGTH: 31
<212> TYPE: DNA
```

<213> ORGANISM: Artificial Sequence
<220> FEATURE:
<223> OTHER INFORMATION: PCR primer
<220> FEATURE:
<221> NAME/KEY: misc_feature
<222> LOCATION: (4)..(9)
<223> OTHER INFORMATION: Kpn I restriction site

<400> SEQUENCE: 22
cccggtacca ctatttataa acaaacatca c                                31

<210> SEQ ID NO 23
<211> LENGTH: 31
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (6)..(11)
<223> OTHER INFORMATION: Xba I restriction site

<400> SEQUENCE: 23
gtaactctag aaggaagtat gatcaatggt a                                31

<210> SEQ ID NO 24
<211> LENGTH: 31
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (4)..(9)
<223> OTHER INFORMATION: Pst I restriction site

<400> SEQUENCE: 24
tatctgcagt ctagttagag aatataatcc a                                31

<210> SEQ ID NO 25
<211> LENGTH: 264
<212> TYPE: DNA
<213> ORGANISM: unknown
<220> FEATURE:
<223> OTHER INFORMATION: native colicin nucleotide sequences

<400> SEQUENCE: 25
gcttcagggc gtgatattgc gatggctata ggaacactat ccgggcaatt tgttgcagga      60
ggaattggag cagctgctgg gggtgtggct ggaggtgcaa tatatgacta tgcatccact     120
cacaaaccta atcctgcaat gtctccatcc ggtttagggg gaacaattaa gcaaaaaccc     180
gaagggatac cttcagaagc atggaactat gctgcgggaa gattgtgtaa ttggagtcca     240
aataatctta gtgatgtttg ttta                                           264

<210> SEQ ID NO 26
<211> LENGTH: 88
<212> TYPE: PRT
<213> ORGANISM: unknown
<220> FEATURE:
<223> OTHER INFORMATION: native colicin amino acid sequences

<400> SEQUENCE: 26

Ala Ser Gly Arg Asp Ile Ala Met Ala Ile Gly Thr Leu Ser Gly Gln
1               5                   10                  15

Phe Val Ala Gly Gly Ile Gly Ala Ala Ala Gly Gly Val Ala Gly Gly
            20                  25                  30

```
Ala Ile Tyr Asp Tyr Ala Ser Thr His Lys Pro Asn Pro Ala Met Ser
        35                  40                  45
Pro Ser Gly Leu Gly Gly Thr Ile Lys Gln Lys Pro Glu Gly Ile Pro
    50                  55                  60
Ser Glu Ala Trp Asn Tyr Ala Ala Gly Arg Leu Cys Asn Trp Ser Pro
65              70                  75                  80
Asn Asn Leu Ser Asp Val Cys Leu
                85
```

EXPRESSION VECTORS FOR TREATING BACTERIAL INFECTIONS

This application is a continuation in part of U.S. Ser. No. 09/883,343 60/054 (filed Jun. 19, 2001); which is a continuation of U.S. Ser. No. 08/924,629 (now U.S. Pat. No. 6,403,082); and a continuation-in-part of U.S. Ser. No.: 10/916,641 (filed Aug. 9, 2004).

I. FIELD OF THE INVENTION

The present invention relates to expression vectors that can be used for transferring at least one heterologous gene into, and expressing it in, a Gram-positive bacterium, preferably a lactic acid bacterium (LAB). The present invention also relates to the anti-bacterial use of the transformed host, the heterologous gene product, fermentate containing the host and/or the gene product, or combinations thereof.

II. BACKGROUND OF THE INVENTION

Many bacteria produce antibacterial peptides or proteins (e.g., bacteriocins) that are generally active against other bacteria, typically closely related. An exemplary list of bacteria and their bacteriocins are shown in Table 1.

The classical bacteriocins are the colicins produced by *Escherichia coli*. Most colicins are relatively large proteinaceous compounds that are not actively secreted from the bacterial cell. Microcins produced by *E. coli* are peptides or polypeptides that are secreted from the cell by a dedicated export pathway and are post-translationally modified (Class I microcins) or are not posttranslationally modified (Class II microcins). Posttranslational modification requires the production of enzymes that modify the ribosomally translated peptide.

Bacteriocins produced by LAB are normally active against other Gram-positive bacteria, especially closely-related LABs. Likewise, bacteriocins produced by Gram-negative bacteria are against Gram-negative target strains. For example, colicin V, a bacteriocin produced by *Escherichia coli*, is active against a wide range of other *E. coli*.

Colicin V was the first colicin discovered from *E. coli*. It is a Class II microcin that is synthesized as a 105 amino acid pre-peptide (leader+bacteriocin) that is cleaved to release the active 88 amino acid mature peptide. The colicin V operon includes a structural gene, an immunity gene, and two dedicated transport genes.

A large number of LAB produce bacteriocins that include the lantibiotic peptides (Class I); non-lantibiotic peptides (Class II); and proteins (Class III). The lantibiotics, e.g., nisin produced by *Lactococcus lactis* subsp. *lactis*, are post-translationally modified and have a genetic operon consisting of about 11 genes for their synthesis, immunity, modification and export from the cell. The non-lantibiotic (Class II) bacteriocins are similar to colicin V in genetic complexity. These bacteriocins are produced as pre-peptides that are cleaved to form the mature peptide and exported from the cell in the same way as colicin V, e.g. carnobacteriocins A and B2, leucocin A, and pediocin PA-1. The non-lantibiotic divergicin A produced by *Carnobacterium divergens* UAL9 requires only two genes for its production and secretion from the cell. Secretion is under the control of the cell's general secretory (sec) pathway. Predivergicin A consists of a signal peptide and divergicin A. One gene or nucleotide sequence encodes a bacteriocin. The other gene encodes an immunity protein.

To date no bacteriocins produced by LAB have been discovered that are active against Gram-negative bacteria, such as *E. coli*. For reasons that will become more evident below, it may be desirable to select a Gram-positive host that produces a bacteriocin active against one or more gram-negative bacteria. For example, LAB could target *E. coli* if it is genetically modified (GMO) to produce a bacteriocin (such as, colicin V) or another bacteriocin that is active against another target bacterium.

Further, the ability to target a Gram-negative bacterium, such as *E. coli*, using a Gram-positive bacterium that expresses a bacteriocin effective against the Gram-negative bacterium, suggests the possibility of an alternative or supplemental therapy or preventative treatment protocol against any diseases or conditions caused by the Gram-negative bacteria. An example of such a condition is post-weaning diarrhea (PWD), also known as scours, which is caused by an *E. coli* infection in pigs.

Outbreaks of *E. coli* PWD or scours are an ongoing problem in pig production. PWD or scours typically result in significant weight loss of the affected animals.

A need exists for treatments that promote weight gain or, at a minimum, result in no further weight loss during infection.

III. SUMMARY OF THE INVENTION

The present invention provides a technology that depends on the use of LAB that are genetically-modified (GMO) to produce heterologous polypeptides, such as bacteriocin(s), that specifically target the causative agent of a disease. One or many specific uses of the compositions and methods of the present invention include treating post weaning diarrhea (PWD) caused by enterotoxigenic *Escherichia coli* in weanling pigs.

This technology can be applied anywhere that Gram-positive LAB grow in a specific environment without causing harm. These environments include animal feed, such as silage; fermented foods and anaerobically- or vacuum-packaged foods, such as raw and processed meats, vegetables and pasta products; and animal (and human) gastrointestinal (GI) or urogenital tracts.

Further, some LAB strains may be probiotic (i.e., health promoting), but they may not be "targeted" against specific pathogens. In accordance with the present invention, some LAB may be targeted by genetic modification against specific pathogens, such as *E. coli*. Still further, the compositions and/or methods of the present invention may be preventative rather than curative. In these embodiments of the invention, the compositions and methods could be effective as a replacement for feeding sub-therapeutic levels of antibiotics as a prophylactic against GI diseases.

The accompanying drawings show illustrative embodiments of the invention from which these and other of the objectives, novel features and advantages will be readily apparent.

IV. BRIEF DESCRIPTION OF THE DRAWINGS

FIG. 5 provides the nucleotide and amino acid sequences of colicin V and colicin VM. FIGS. 5A and 5C show the nucleotide and amino acid sequences of colicin V, respectively; and FIGS. 5B and 5D show the nucleotide and amino acid sequences of colicin VM, respectively.

Figure 6:
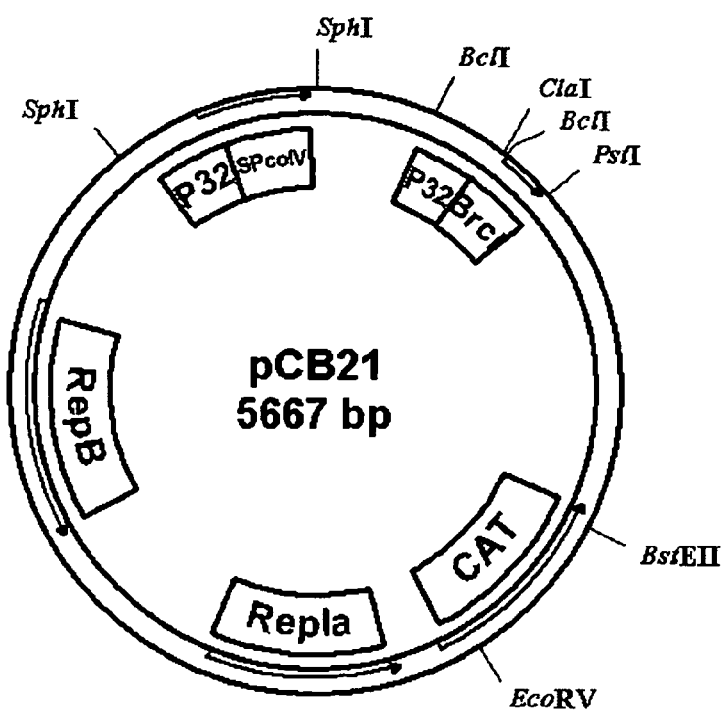

FIG. 6 is a schematic representation of pCB21, and illustrates the removal of the EcoRV restriction site from pCB15.

Figure 7:
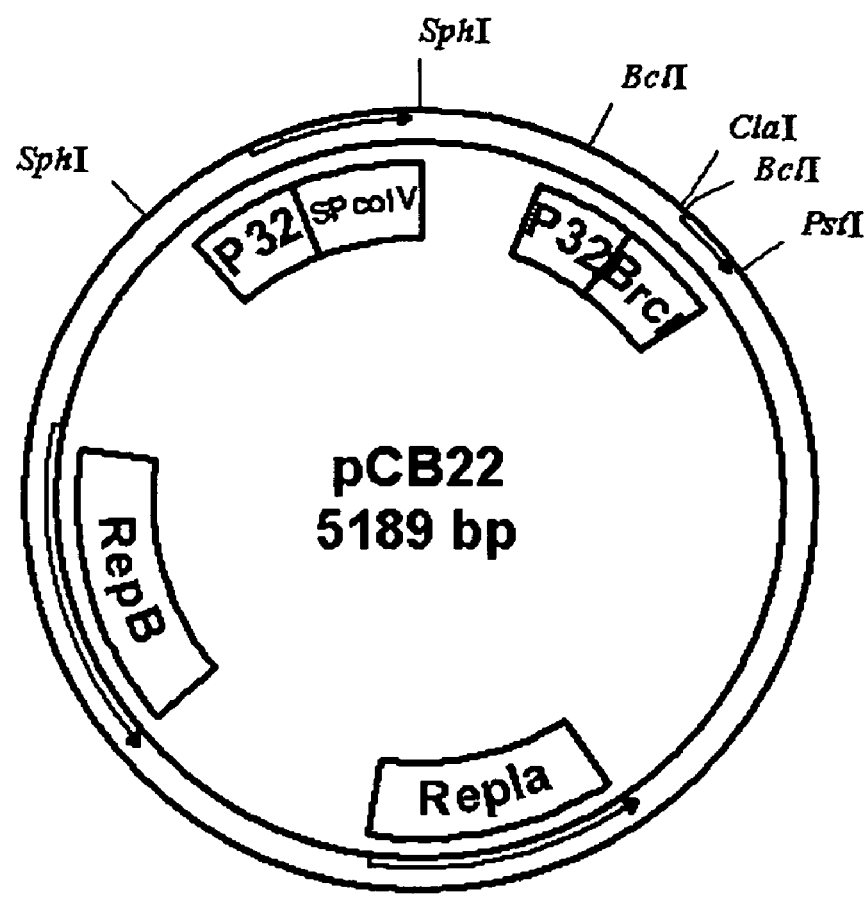

FIG. 7 is a schematic representation of pCB22, and illustrates the removal of the cat gene from pCB21.

Figure 8:
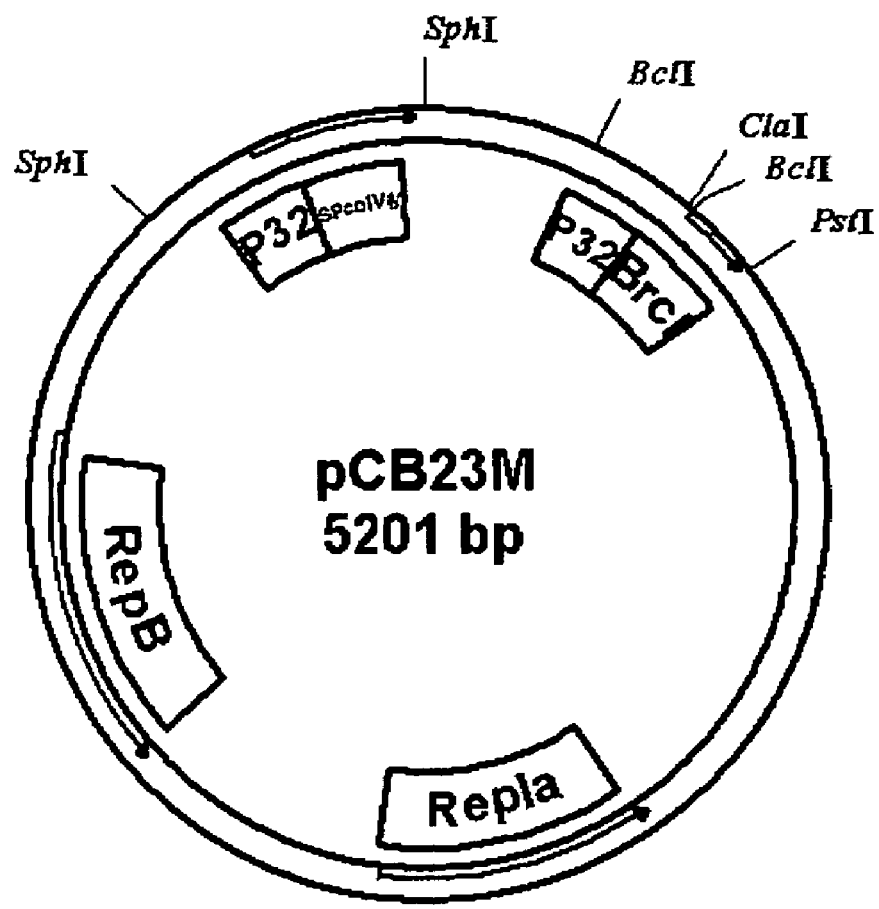

FIG. 8 is a schematic representation of pCB23m, and of a feed-grade vector; and illustrates the change of the colicin V gene in pCB22 to a colicin VM gene (col VM) in pCB23m.

Figure 9:
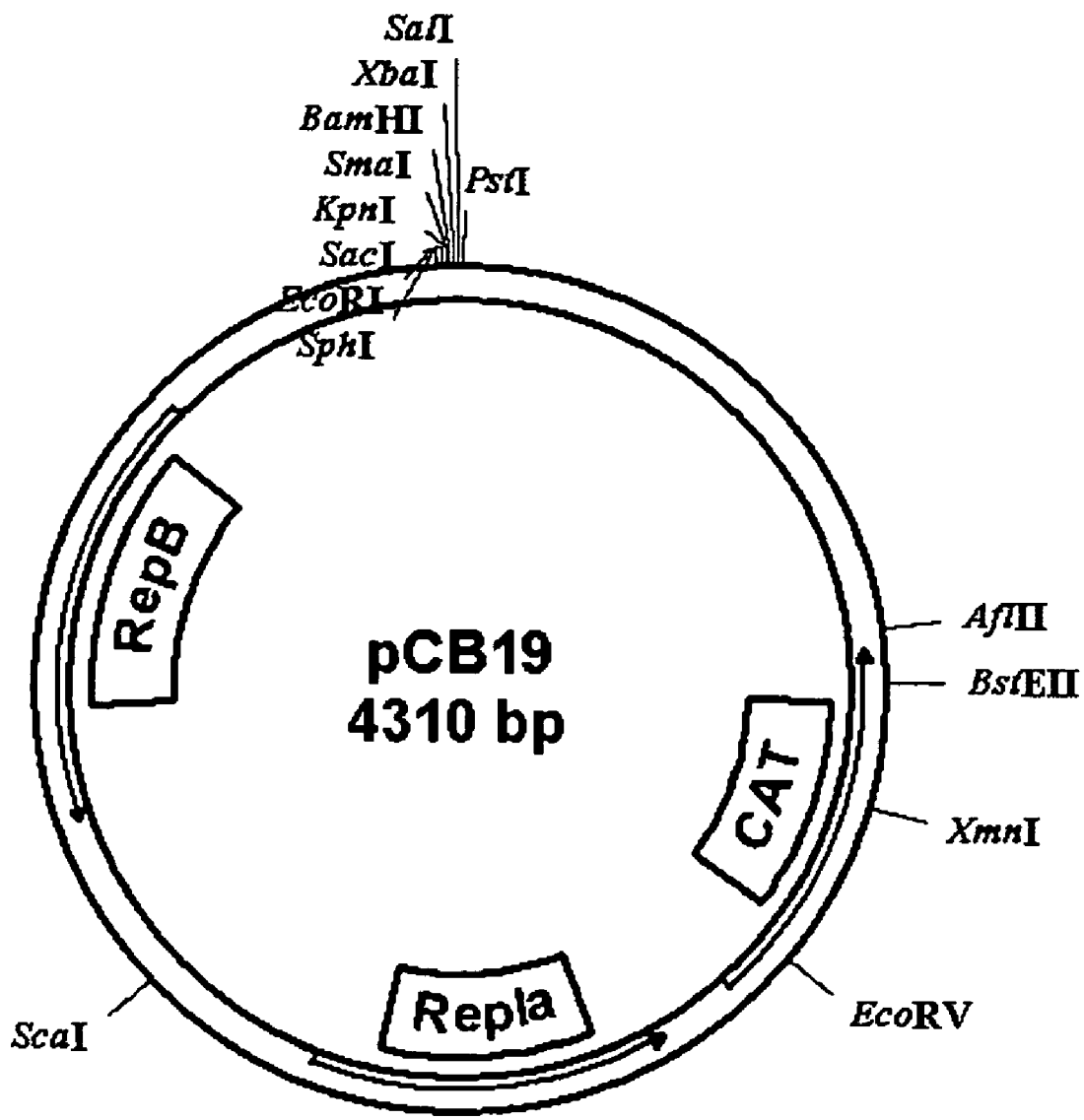

FIG. 9 is a schematic representation of pCB19, and graphically illustrates the inclusion of a polylinker containing multiple cloning sites.

FIG. 10 is the nucleotide sequence of the p15 promoter.

Figure 11:
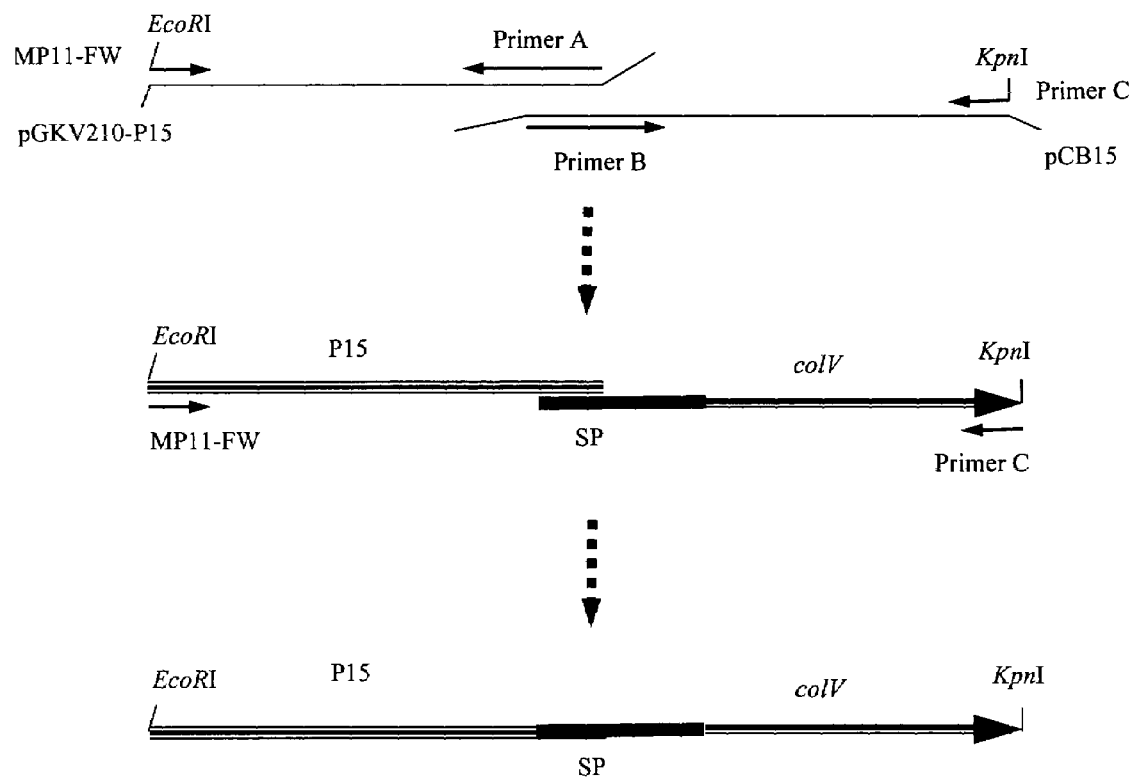

FIG. 11 is a schematic representation of the recombinant PCR technique used to generate the DNA fragment containing the p15 promoter and colicin v gene. The restriction sites (EcoRI and KpnI) and the primers used are labeled. pGKV210-p15 and pCB15 were used as templates for the first round of PCR. SP=signal peptide divergicin A; colV=colicin V gene; p15=p15 promoter.

Figure 12:
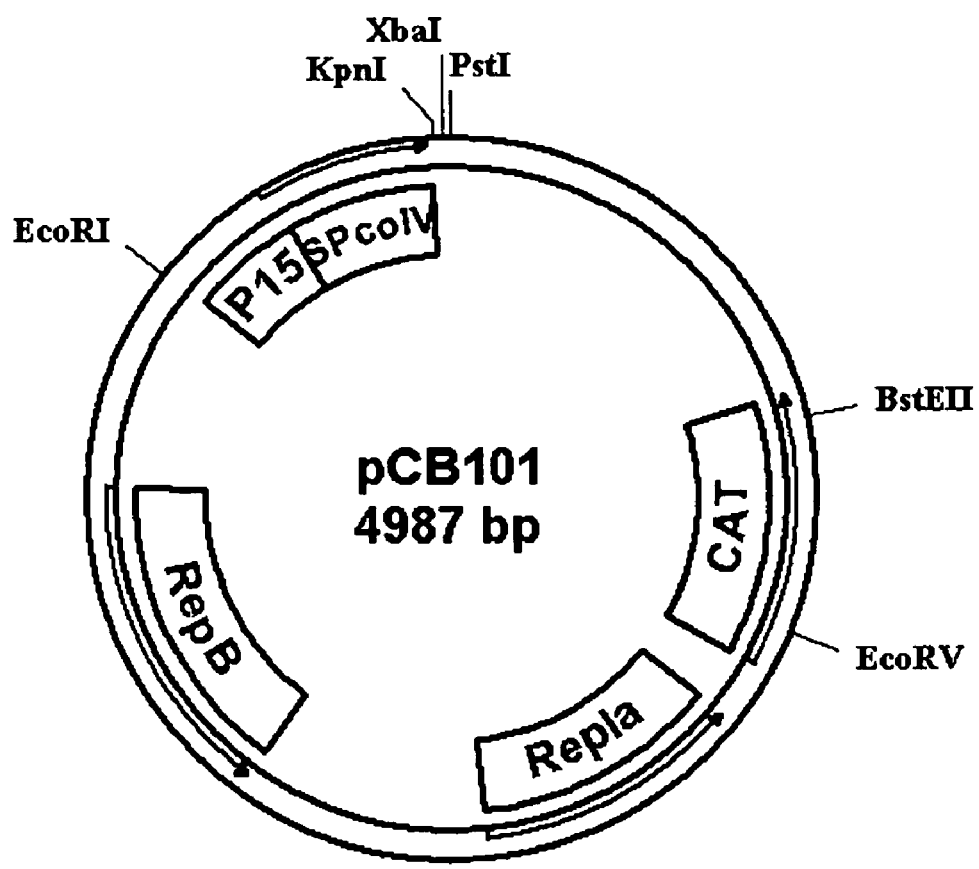

FIG. 12 is a schematic representation of pCB101.

Figure 13:
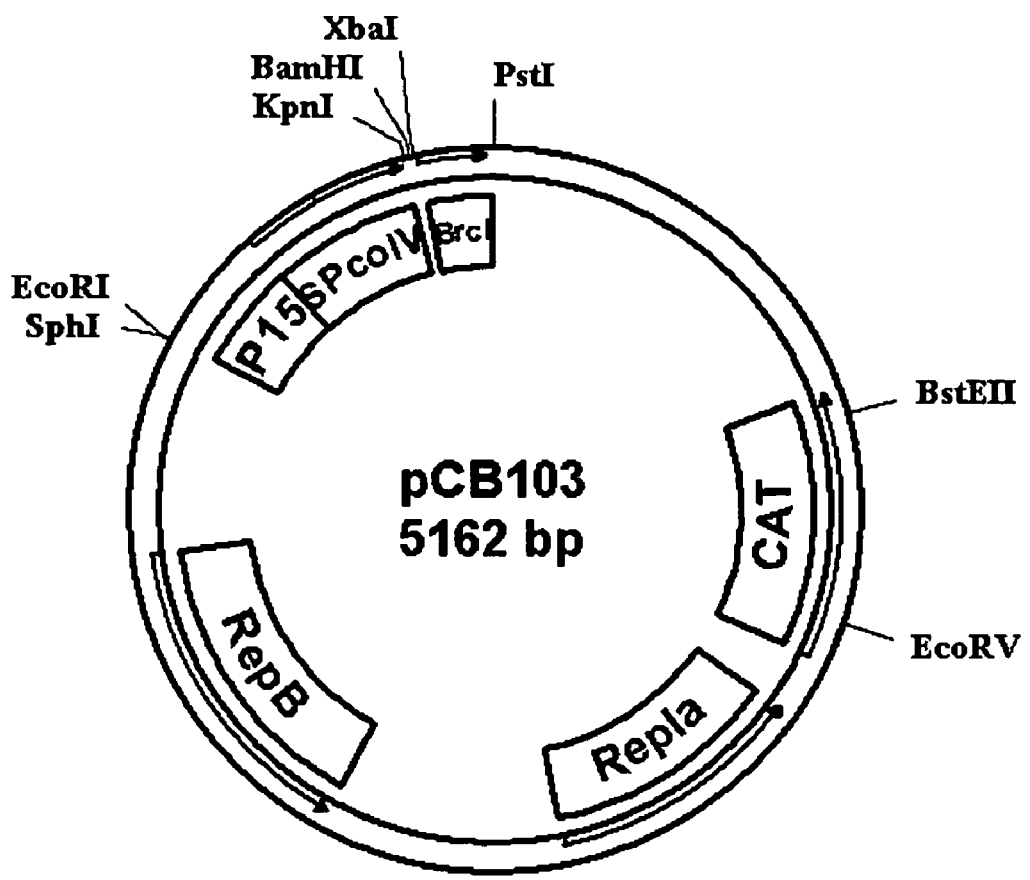

FIG. 13 is a schematic representation of pCB103.

Figure 14:
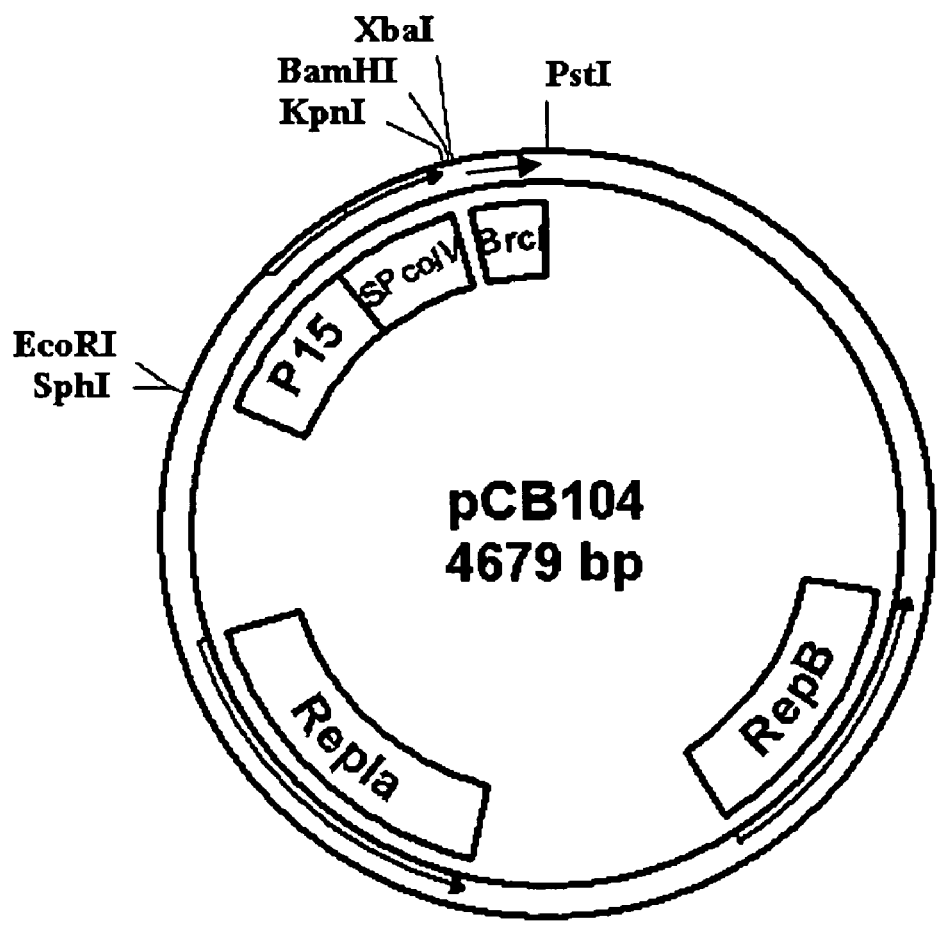

FIG. 14 is a schematic representation of pCB104.

Figure 15:
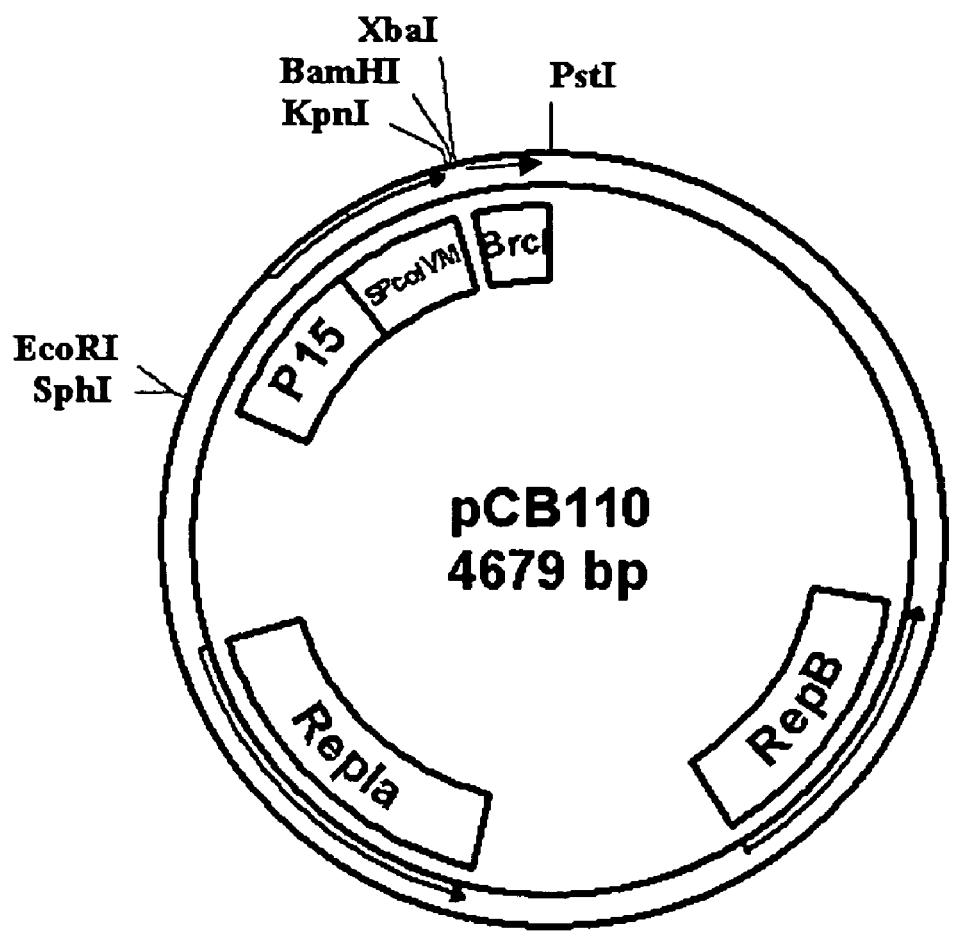

FIG. 15 is a schematic representation of pCB110.

Figure 16:
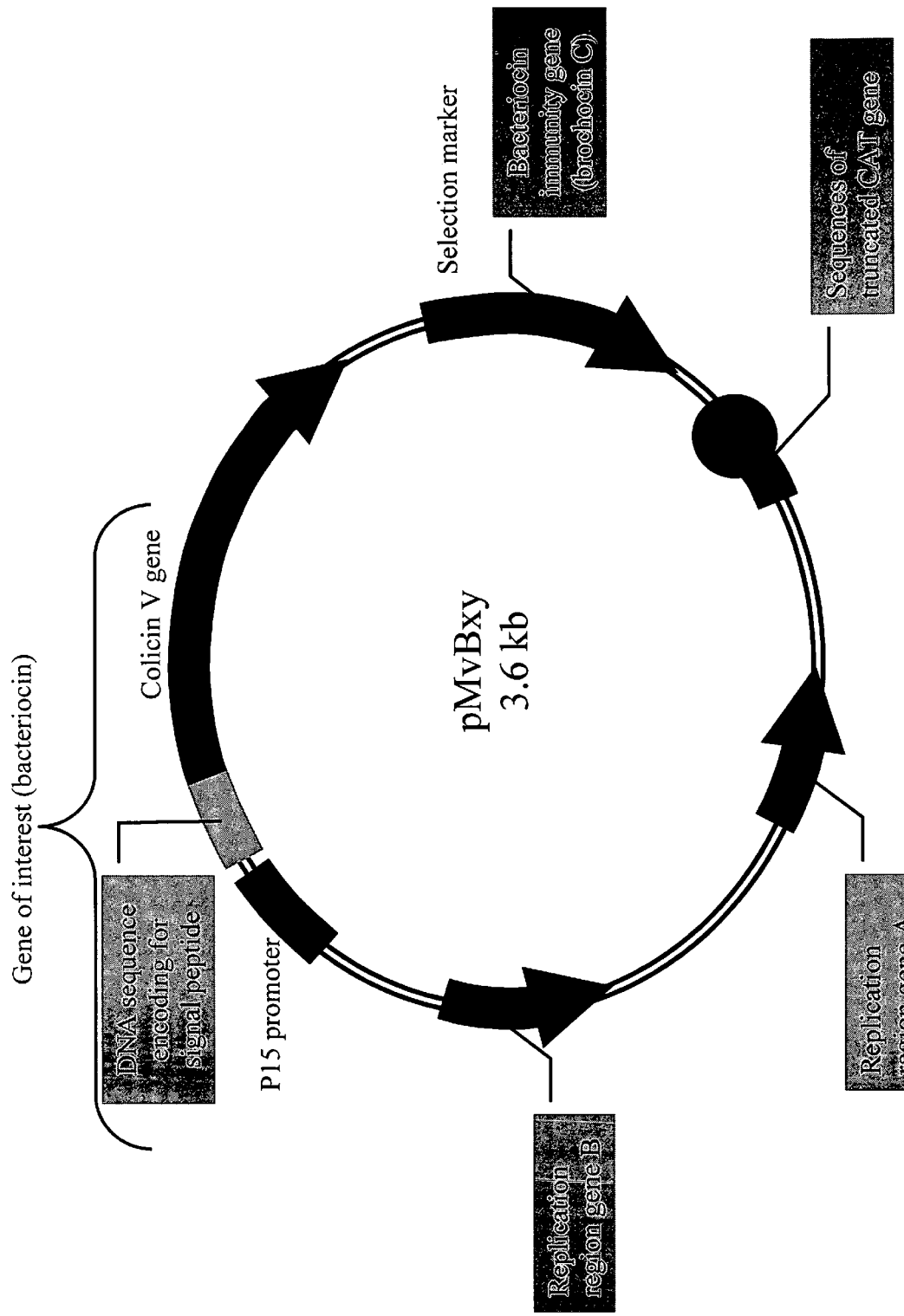

FIG. 16 illustrates an expression vector pMvB of the present invention.

V. DETAILED DESCRIPTION OF THE INVENTION

The present invention is compositions and methods for expressing a gram (−) polypeptide, such as a bacteriocin, in a Gram-positive host, such as a lactic acid bacterium. The invention also includes the use of a Gram-positive host, genetically modified according to the present invention, the polypeptide produced by the genetically modified host, compositions that include the GMO bacterium and/or the polypeptide, and combinations thereof in the treatment of susceptible bacteria.

The present invention also includes an expression vector suitable for transforming a Gram-positive host and secreting a polypeptide effective against a Gram-negative bacterium. In these embodiments of the invention, one skilled in the art will readily recognize that the expression vector may be variously configured according to the choice of host, promoter, and polypeptides used. In preferred embodiments of the present invention, the expression vectors include a signal peptide, preferably a divergicin A signal peptide, and at least one bacteriocin immunity gene. In the most preferred embodiments of the invention, the expression vector is suitable for use in a LAB host.

The present invention also includes compositions and methods for treating susceptible bacteria and the diseases or conditions caused by the susceptible bacteria. In a preferred embodiment of the invention, some of the compositions and methods of the present invention are used to treat *E. coli*. In the most preferred embodiments of the invention, the compositions and methods are used to treat scours.

An embodiment of the present invention includes expression vectors for expressing a mutant colicin V bacteriocin (termed colicin VM). In this embodiment of the invention, the expression vector comprises nucleotide sequences that encode colicin VM. Exemplary nucleotide sequences include but are not limited to those shown in Seq. I.D. No. 1 and Seq. I.D. No. 3. Exemplary amino acid sequences include but are not limited to those shown in Seq. I.D. No. 2 and Seq. I.D. No. 4. One skilled in the art will recognize that various promoters signal peptides, selection markers, and other conventional elements of a functional expression vector may be used to express colicin VM.

An exemplary embodiment of the invention comprises a pCB vector comprising a P15 or P32 promoter; a divergicin A signal peptide; nucleotide sequences encoding a colicin VM; a selection marker, including but not limited to a bacteriocin immunity gene (such as brochocin-C); and a suitable replication region or regions. In the expression vector shown in FIG. 4, the expression vector includes a P32 promoter, a divergicin A signal peptide, nucleotide sequences encoding colicin VM, nucleotide sequences encoding a brochocin-C immunity gene, and the replication regions Rep1A and RepB from pCaT (see Jewell, et al.; Current Microbiology: 19:343-346 (1989)).

In preferred embodiments of the invention, the expression vector and the host transformed by the expression vector are food or feed-grade. In the most preferred embodiments of the invention, the host and the expression vector do not contain a gene or nucleotide sequence that encodes or confers antibiotic resistance.

Another embodiment of the present invention includes a host cell transformed by an expression vector of the present invention. In a preferred embodiment of the invention, the compositions and methods include CB4, a *Lactobacillus reuteri* host transformed with expression vector pCB15s that contains nucleotide sequences encoding colicin VM bacteriocin. CB4 was deposited in the American Type Culture Collection (10801 University Boulevard, Manassas, Va. USA 20118) on 8 Dec. 2004, and received Accession No. PTA-6426.

In these embodiments of the invention, host lactic acid bacteria are capable of expressing or secreting one or more polypeptides, including one or more bacteriocins, and include an expression vector as described herein that permit the secretion of one or more bacteriocins. The expression vector may be introduced into the host bacterium by conjugation, transformation, protoplast fusion, or other gene or nucleotide transfer method.

Another embodiment of the present invention includes an expression vector and methods of use thereof wherein the vector includes a bacteriocin immunity gene selected from the group consisting of, but not limited to, brochocin-C and carnobacteriocin A.

Another embodiment of the present invention includes an animal feed comprising a host bacterium transformed with an expression vector of the present invention, a bacterium produced by a transformed host of the present invention, or combinations thereof.

Another embodiment of the present invention includes a probiotic composition comprising a host bacterium transformed with an expression vector of the present invention, a bacteriocin produced by a transformed host of the present invention, or combinations thereof.

Another embodiment of the present invention includes a method of treating bacterial infections in animals or humans using a composition comprising a host bacteria transformed with an expression vector of the present invention, a bacteriocin produced by a transformed host of the present invention, or combinations thereof.

Another embodiment of the present invention includes compositions and methods for treating any *E. coli* susceptible to a bacteriocin expressed in accordance with the present invention. Preferred embodiments of the invention include treating *E. coli* and/or the diseases and conditions caused by *E. coli*. The most preferred embodiments of the invention include treating post-weaning diarrhea or scours, and/or promoting weight gain or preventing weight loss, in pigs.

An expression vector of the present invention may be derived from LAB, in particular LAB of the genus *Lactobacillus*. The plasmids according to the invention can advantageously be stably transferred into lactic acid bacteria that belong to the genera *Carnobacterium, Leuconostoc, Lactobacillus, Pediococcus*, or *Enterococcus*, among others.

The invention also relates to a plasmid or host transformed with the plasmid, as previously defined, the plasmid comprising the nucleotide sequence SEQ ID No. 1, or Seq. I.D. No. 3, or a sequence which differs from this sequence by the insertion, deletion or mutation of from one to several base pairs, and which retains the ability to replicate. The invention also relates to a plasmid or host transformed with the plasmid, as previously defined, the plasmid expressing the amino acid sequence comprising Seq. ID No. 2, or Seq. I.D. No. 4, or a sequence which differs from this sequence by the insertion, deletion or mutation of one to several amino acids, and which retains the ability to replicate.

The invention also relates to an expression vector as shown in FIGS. 2-4, 6-9, and 12-15, the vector comprising the nucleotide sequence or sequences as shown, or a sequence which differs from this sequence by the insertion, deletion or mutation of one or several base pairs and which retains the ability of the plasmid to replicate stably in suitable bacterial host cells, e.g., LAB.

The invention also relates to bacterial host cells that comprise an expression vector according to the invention. Exemplary expression vectors of the present invention include but are not limited to pJKM37, pCV22, pCB12, pCB15, pCB15s, pCB21, pCB22, pCB23M, pCB19, pGKV210, pGKV210-P15, pCB101, pCB103, pCB104, pCB110, and pCB111. Exemplary hosts transformed by at least one of these expression vectors include but are not limited to *Carnobacterium maltaromaticum* UAL26, *Lactobacillus reuteri* CB4, two other strains of *Lactobacillus reuteri* and one strain of *Lactobacillus johnsonii*.

Because of the breadth of host cells that can be used for transformation purposes, the plasmids according to the present invention constitute outstanding tools for cloning and expressing heterologous nucleotide sequences in host LAB.

In particular, the plasmids according to the invention can be used for expressing heterologous proteins, such as bacteriocins, and proteins for resistance to these bacteriocins, also termed immunity proteins.

Each of these elements will now be described in more detail.

In accordance with the present invention, any suitable host bacterium may be used. In preferred embodiments of the invention, the host bacterium is a Gram-positive bacterium. In the most preferred embodiments of the invention, the host bacterium is a lactic acid bacterium (LAB). Exemplary suitable host include, but are not limited to, those shown in Table 1 and in the Examples. The choice of a suitable host is well within the skill of one skilled in the art.

In preferred embodiments of the invention, the host is *L. reuteri*. In the most preferred embodiments of the invention, the host is CB4, a *Lactobacillus reuteri* strain.

In accordance with the present invention, any promoter suitable for use with expressing a bacteriocin gene may be used. For example, any promoter may be employed that is compatible with the host strain in which the secretion system of the present invention is used. Suitable promoters and the choice of a particular promoter are apparent to one skilled in the art. Suitable exemplary promoters include but are not limited to P15 and P32. See for example U.S. Pat. No. 5,939,317, incorporated herein by reference. In preferred embodiments of the invention, the expression vector includes a P15 promoter, operatively associated with the bacteriocin gene of interest. In accordance with the present invention, a promoter having nucleotide sequences corresponding to Seq. ID No. 5 may be used (see FIG. 10).

In accordance with the present invention, any signal peptide suitable for use with expressing a bacteriocin gene may be used. Suitable signal peptides include, but are not limited to, a signal peptide of divergicin A. In preferred embodiments of the invention, the expression vector includes a divergicin A signal peptide, operatively associated with the bacteriocin gene of interest. In accordance with the present invention, a divergicin A signal peptide having nucleotide sequences corresponding to those disclosed in U.S. Pat. No. 6,403,082 (Stiles et al.), incorporated herein by reference, may be used.

In accordance with the present invention, any bacteriocin gene may be used. See, for example, Table 1. Suitable bacteriocin genes include but are not limited to colicin V, colicin Y101, colicin VM, leucocin A, and brochocin-C. In preferred embodiments of the invention, the expression vector includes a nucleotide sequence or gene encoding one of more of the above bacteriocins. In the most preferred embodiments of the invention, the expression vector comprises nucleotide sequences or a gene encoding colicin VM. Exemplary nucleotide sequences for a bacteriocin are well known to those skilled in the art. See, for example, U.S. Pat. No. 6,403,082 (Stiles, et al.).

In accordance with the present invention, the compositions and methods include a host and/or an expression vector that comprises nucleotide sequences or a gene that encodes a mutated colicin V that contains the following nucleotide sequence: gtggctggaggtgtggctggaggt (Seq. I.D. No. 1). See FIG. 5B. In a most preferred embodiment of the invention, the compositions and methods include a host and/or an expression vector that comprises nucleotide sequences or a gene that encodes a mutated colicin V that contains the nucleotide sequences shown in FIG. 5B (Seq., I.D. No. 3).

In accordance with the present invention, the compositions and methods include a host and/or an expression vector that encodes the following colicin VM amino acid sequence: VAGGVAGG (Seq. I.D. No. 2). In a most preferred embodiment of the invention, the compositions and methods include a host and/or an expression vector that encodes A colicin VM amino acid sequence corresponding to (Seq. I.D. No. 4). See FIG. 5D.

In accordance with the present invention, any selection marker suitable for use with expressing a bacteriocin gene may be used. Suitable selection markers include but are not limited to immunity genes for carnobacteriocin A, piscicolin 126, and brochocin-C; and antibiotic resistance genes, e.g., chloramphenicol, erythromycin, and streptomycin. In preferred embodiments of the invention, the expression vector includes a bacteriocin immunity gene, preferably a brochocin C immunity gene, operatively associated with the bacteriocin gene of interest. Exemplary nucleotide sequences for an immunity gene are well known to those skilled in the art. See, for example, U.S. Pat. No. 6,403,082 (Stiles, et al.), incorporated herein by reference. As noted above, it may be highly desirable to produce and use a feed-grade vector and host; such vectors and host lack functional antibiotic resistance genes and, in accordance with the present invention, include nucleotide sequences or genes that encode bacteriocin immunity.

The invention also includes a method of treating a bacterial infection or a method of treating an animal (including a human) by administering or contacting the bacteria or animal with one or more of the following compositions: a composition comprising one or more hosts transformed by an expression vector of the present invention; a composition comprising one or more bacteriocins produced by a transformed host; one or more bacteriocins produced naturally or by GMO (see, for example Table 1); or combinations thereof.

In preferred embodiments of the invention, any of the compositions of the present invention may be used to treat an *E. coli* disease or condition, including but not limited to scours. In some embodiments of the invention, any of the compositions of the present invention may be used to promote weight gain in the subject animal. In some embodiments of the present invention, any of the compositions of the present invention may be used to treat or affect indigenous microflora in the treated subject.

An embodiment of the present invention includes expression vector pMvB, comprising a suitable promoter, e.g., P15; a signal peptide encoding DNA, e.g., divergicin A signal peptide; a gene encoding a polypeptide, e.g., encoding a bacteriocin, including but not limited to colicin V; a selection marker, including but not limited to a bacteriocin immunity gene, e.g., brochocin C; and a suitable replication region or regions, e.g., pCaT (a commercially available plasmid).

In preferred embodiments of the invention, sequences from a pCaT plasmid that is not required and/or unwanted (such as antibiotic markers and mobilization genes) are deleted to result in a fragment of pCaT that may be used as a replicon. In accordance with the present invention, several additions are made to the pCaT replicon, including but not limited to any desired genes (such as bacteriocin and immunity genes), promoters (such as P15) and expression signals. In accordance with the present invention, a replication sequence (or replication sequences) suitable for use in a lactic acid bacteria host may be used. Suitable replication sequences include but are not limited to the replication region(s) of pCaT. In preferred embodiments of the invention, the replication sequences include a pCaT segment derived from *L. plantarum*.

Definitions

The term "gene" as used herein refers to a DNA sequence, including but not limited to a DNA sequence that can be transcribed into mRNA which can be translated into polypeptide chains, transcribed into rRNA or tRNA or serve as recognition sites for enzymes and other proteins involved in DNA replication, transcription and regulation. These genes include, but are not limited to, structural genes, immunity genes and secretory (transport) genes.

The term "vector" as used herein refers to any DNA material capable of transferring genetic material into a bacterial host organism. The vector may be linear or circular in topology and includes but is not limited to plasmids, food grade plasmids or bacteriophages. The vector may include amplification genes, enhancers or selection markers and may or may not be integrated into the genome of the host organism. The term "secretion vector" or "expression vector" refers to a vector designed to provide secretion of a polypeptide such as a protein from the host organism.

The term "signal peptide" as used herein refers to amino-terminal amino acid residues that, when attached to a target polypeptide, permits the export of the target polypeptide from the cell and cleavage of the signal peptide. The signal peptide accesses the general protein secretion pathway. An example of a signal peptide is the Divergicin A signal peptide described in U.S. Pat. No. 6,403,082, incorporated herein by reference. Other signal peptides can be used and are known to those skilled in the art.

The term "feed or food-grade" as used herein refer to the origin of the DNA material and its constituents. Food-grade indicates that a regulatory agency would consider the substance as coming from a food source and therefore suitable for inclusion in food or food products, typically those intended for human or animal consumption. Organisms that are food-grade, such as lactic acid bacteria and other established genera of starter organisms, can be added directly to food without concern for pathogenicity. Food or feed grade as used herein also refers to the quality of a substance, specifically whether it is free of elements or the like that might be undesirable. A food or feed grade expression vector or a food or feed grade bacterium of the present invention is free of or lacks an antibiotic resistance gene, or is free of or lacks an expressible or functional antibiotic resistance gene. In preferred embodiments, the food or feed grade compositions of the present invention may be used in or comprise silage, foods, feeds, diary products, meat, vegetables, or pasta.

The term a "bacteriocin" as used herein refers to polypeptides and the like produced by the bacteria that inhibit one or more bacterial species. This includes, but is not limited to, polypeptides that are derived from specific strains of bacteria, proteins that are derived from other types of organisms, or proteins developed through genetic engineering. The bacteriocin can be bacteriostatic or bactericidal.

The term "immunity gene" as used herein refers to a gene that produces a protein that protects the host organism against the bacteriocin that it produces. An immunity gene may also be used as a selection marker.

The term "susceptible bacterium" as used herein refers to a species or strain of bacteria that is inhibited by the presence of one or more bacteriocins in its environment.

Although the present invention has been described in terms of particular preferred embodiments, it is not limited to those embodiments. Alternative embodiments, examples, and modifications that would still be encompassed by the invention may be made by those skilled in the art, particularly in light of the foregoing teachings.

TABLE 1

| Strain | Bacteriocin |
|---|---|
| Our lab collection of LAB | |
| 1. *Carnobacterium maltaromaticum* CB1 | carnobacteriocin BM1, piscicolin 126 + unknown |
| 2. *C. maltaromaticum* CB2 | carnobacteriocin BM1, piscicolin 126 + unknown |
| 3. *C. maltaromaticum* CB3 | carnobacteriocin BM1, piscicolin 126 |
| 4. *C. maltaromaticum* UAL26 | piscicolin 126 |
| 5. *C. maltaromaticum* LV17 | carnobacteriocin A, BM1 and B2 |
| 6. *C. maltaromaticum* UAL26/8A | piscicolin 126, carnobacteriocin A |
| 7. *Carnobacterium divergens* LV13 | divergicin A |
| 8. *Leuconostoc gelidum* UAL187 | leucocin A |
| 9. *Lactobacillus sakei* UAL185 | unknown |
| 10. *Leuconostoc* spp. UAL280 | unknown |
| Non-LAB inhibiting *Listeria* spp. | |
| 11. *Brochothrix campestris* ATCC43754 | brochocin C |
| 12. *Staphylococcus aureus* A53 | aureocin A53 |
| 13. *Brevibacterium linens* ATCC9175 | unknown |
| 14. *B. linens* OC2 | linenscin 002 |
| 15. *Bifidobacterium bifidum* NCFB1454 | bifidocin B |

TABLE 1-continued

| Strain | Bacteriocin |
|---|---|
| Meat applied LAB inhibiting Listeria | |
| 16. C. maltaromaticum LV61 | carnobacteriocin A |
| 17. C. maltaromaticum V1 | carnobacteriocin BM1, piscicolin 126 |
| 18. C. maltaromaticum CP5 | carnobacteriocin BM1 and B2 |
| 19. C. maltaromaticum JG126 | piscicolin 126 |
| 20. Carnobacterium spp. 377 | carnocin H |
| 21. C. maltaromaticum U149 | carnocin U149 |
| 22. C. divergens 750 | divergicin 750 |
| 23. Pediococcus acidilactici PAC1.0 | pediocin PA-1 |
| 24. P. acidilactici E | pediocin PA-1 |
| 25. P. acidilactici F | pediocin PA-1 |
| 26. P. acidilactici H | pediocin PA-1 |
| 27. P. acidilactici JD1-23 | pediocin PA-1 |
| 28. P. acidilactici M | pediocin PA-1 |
| 29. P. pentosaceous Z102 | pediocin PA-1 |
| 30. Lactobacillus plantarum WHE92 | pediocin PA-1 |
| 31. L. plantarum ALC01 | pediocin PA-1 |
| 32. Lactobacillus sakei Lb706 | sakacin A |
| 33. Lb. sakei CTC494 | sakacin A |
| 34. Lactobacillus curvatus LTH1174 | sakacin A |
| 35. Lb. sakei LTH673 | sakacin P |
| 36. Lb. sakei 674 | sakacin P |
| 37. Lactobacillus bavaricus M1401 | sakacin P |
| 38. Lb. sakei MN | bavaricin MN |
| 39. Enterococcus faecium CTC492 | enterocin A and B |
| 40. E. faecium T136 | enterocin A and B |
| 41. E. faecium WHE81 | enterocin A and B |
| 42. E. faecium BFE900 | enterocin A and B |
| 43. E. faecium L50 | enterocin L50A and L50B, P, Q |
| 44. E. faecium DPC1146 | enterocin A |
| 45. E. faecium EK13 | enterocin A and P |
| 46. E. faecium P13 | enterocin P |
| 47. E. faecium AA13 | enterocin P |
| 48. E. faecium G16 | enterocin P |
| 49. E. faecium JCM5804T | enterocin A, B, P |
| 50. Enterococcus casseliflavusIM416K1 | enterocin 416K1 |
| 51. Leuconostoc carnosum 4010 | leucocin A and C |
| 52. Lb. plantarum UG1 | plantaricin UG1 |
| 53. E. faecium CRL35 | enterocin CRL35 |
| 54. Lactobacillus casei CRL705 | lactocin CRL705 |
| 55. Lb. sakei CTC494 | sakacin K |
| 56. L. carnosum | leucocin F10 |
| 57. L. carnosum | leucocin B-Ta11a |
| 58. Lactobacillus brevis VB286 | brevicin 286 |
| 59. Lb. plantarum CTC305 | unknown |
| 60. Lb. plantarum CTC306 | unknown |
| 61. Lb. sakei CTC372 | unknown |
| LAB inhibiting Listeria | |
| 62. C. maltaromaticum CS526 | unknown |
| 63. Streptococcus thermophilus Sfi13 | thermophilin 13 |
| 64. E. faecalis EJ97 | enterocin EJ97 |
| 65. E. faecalis BFE1071 | enterocin 1071 |
| 66. E. faecalis FAIR-E309 | enterocin 1071 |
| 67. E. faecalis Y1717 | bacteriocin 31 |
| 68. E. faecalis LMG2333 | enterolysin A |
| 69. E. faecalis DPC5280 | enterolysin A |
| 70. E. faecalis S-48 | enterocin AS-48 |
| 71. E. faecalis INIA4 | enterocin AS-48 |
| 72. Lb. plantarum ALC01 | pediocin PA-1 |
| 73. Lb. sake 2512 | sakacin G |
| 74. Lb. plantarum 423 | plantaricin 423 |
| 75. Enterococcus mundtii ATO6 | mundticin |
| 76. E. mundtii NFR17393 | mundticin KS |
| 77. Lactobacillus buchneri | buchnericin-LB |
| 78. L. lactis MMFII | lactococcin MMFII |
| 79. L. lactis UL720 | diacetin B |
| 80. Enterococcus galilnarum 012 | enterocin 012 |
| 81. Lb. plantarum | plantaricin NA |
| 82. Leuconostoc mesenteroides FR52 | mesenterocin 52A |
| 83. L. mesenteroides Y105 | mesentericinY105 |
| ILantibiotics inhibiting Listeria | |
| 84. L. lactis | nisin |
| 85. L. lactis | nisin Z |
| 86. L. lactis 61-14 | nisin Q |
| 87. L. lactis DPC3147 | lacticin3147 |
| Other bacteriocin producing bacteria | |
| 88. L. lactis | lactococcin A, B, M |
| 89. L. lactis LMG280 | lactococcin G |
| 90. L. lactis IPLA972 | lactococcin 972 |
| 91. L. lactis DPC5552 | lacticin 481 |
| 92. L. lactis BGMN1-5 | LsbA, LsbB |
| 93. Lactobacillus johnsoniiVPI11088 | lactacin F |
| 94. Lactobacillus acidophilus M46 | acidocin B |
| 95. Lb. acidophilus N2 | lactacin B |
| 96. Lactobacillus gasseri LA39 | gassericin A |
| 97. Lactobacillus salivarius UCC118 | ABP-118 |
| 98. L. plantarum C11 | plantaricin E/F, J/K |
| 99. L. plantarum NC8 | plantaricin NC8 |
| 100. Propionibacterium jensenii DF1 | propionicin SM1 |
| 101. Escherichia coli | colicin V |
| 102. E. coil | colicin Y101 |
| 103. E. coli | microcin H47 |
| 104. Staphylococcus epidermis | epidermin |
| 105. Bacillus subtilis 168 | subtilosin A |
| 106. Lb. gasseri | gassericin K7B |
| 107. Klebsiella pneumoniae | microcin E492 |
| 108. Ciostridium tyrobutyricumADRIAT932 | closticin574 |
| 109. Clostridium beijerinckii ATCC25752 | circularin A |
| 110. Lactobacilius amylovorus DCE471 | amylovorin L471 |
| 111. Lb. plantarum SA6 | plantaricin SA6 |
| 112. Lb. sakei L45 | lactocinS |
| The following bacteriocins are called microcins produced by gram-negative bacteria: | |
| 1. Klebsiella pneumoniae RYC492 | microcin E492 (same as 107) |
| 2. E. coli | microcin V (same as 101, colicin is "old" name) |
| 3. E. coli | microcin Y101 (same as 102) |
| 4. E. coli | microcin H47 |
| 5. E. coli | microcin L |
| 6. E. coli | microcin 24 |

EXAMPLES

The following examples are provided as a guide for those skilled in the art to carry out the invention.

GENERAL MATERIALS AND METHODS

*Escherichia coli* DH5α cells were grown in Luria Broth (LB) medium (Difco Laboratories Inc.) at 37° C.; *Carnobacterium maltaromaticum* UAL26 was grown in APT (All Purpose Tween) medium (Difco) at 25° C.; and *Lactobacillus reuteri* CB4 was grown in Lactobacilli MRS medium (MRS; Difco) at 37° C. Bacteriocin production was tested as described previously (van Belkum and Stiles, 1995). Colicin V production was tested using *E. coli* (DH5α) as the indicator organism grown on APT medium supplemented with 1.5% (wt/vol) agar for solid plating. Selective concentrations of chloramphenicol for growth of UAL26 and CB4 containing recombinant plasmids were 5 and 10 μg/ml, respectively. Cloning and DNA manipulations were performed as described by Sambrook et al. (1989). Enzymes used for molecular cloning were obtained from Invitrogen and used as specified by the manufacturer. Plasmid isolation was done as described by van Belkum and Stiles (1995). Nucleotide sequencing was based on the method of Sanger et al. (1977) and done in a Perkin-Elmer ABI-Prism DNA sequencer with fluorescent chain terminators. For transformation of UAL26 and CB4, cells were grown in APT or MRS medium supplemented with 2% (wt/vol) glycine, respectively. Exponentially growing cells were harvested and washed twice with ice-cold water and twice with ice-cold electroporation buffer (0.5 M sucrose, 10% glycerol, 1 mM $MgCl_2$, 5 mM potassium phosphate buffer [pH6] and concentrated 100-fold in the same buffer. Cells were divided into 50 µl portions and stored at −70° C. Electroporation was done as described by van Belkum and Stiles (1995) with the following modification for CB4: cells were incubated at 44° C. for 20 min and chilled on ice for an additional 10 min prior to the addition of DNA. Electroporation was done in a Gene-Pulser instrument (Bio-Rad). One pulse of 25 µF, 200 Ω, 2.5 kV was used for UAL26 and one pulse of 25 µF, 800 Ω, 1.0 kV for CB4.

Example 1

Use of Plasmid pCaT and its Derivatives as Cloning Vectors in LAB

Figure 1:
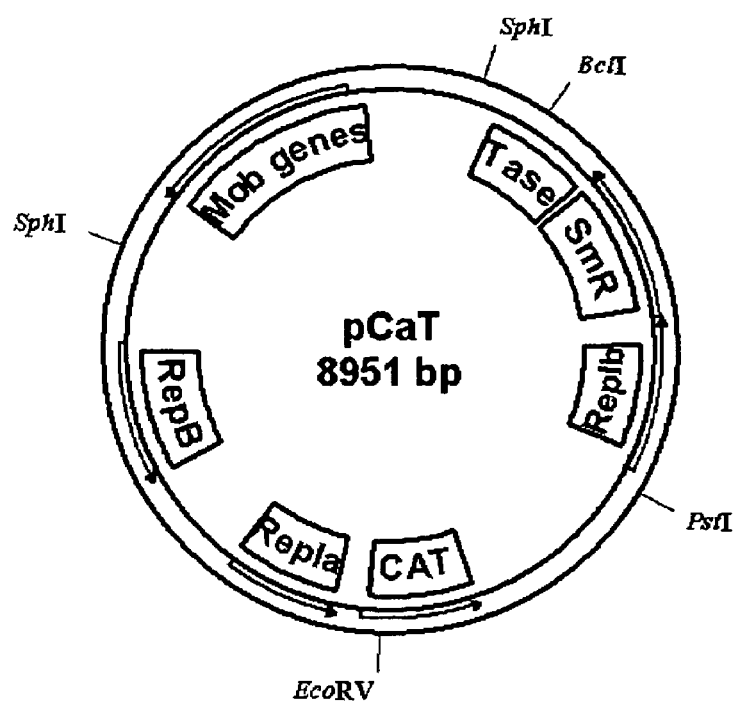
FIG. 1 is a schematic representation of pCaT.
Figure 2:
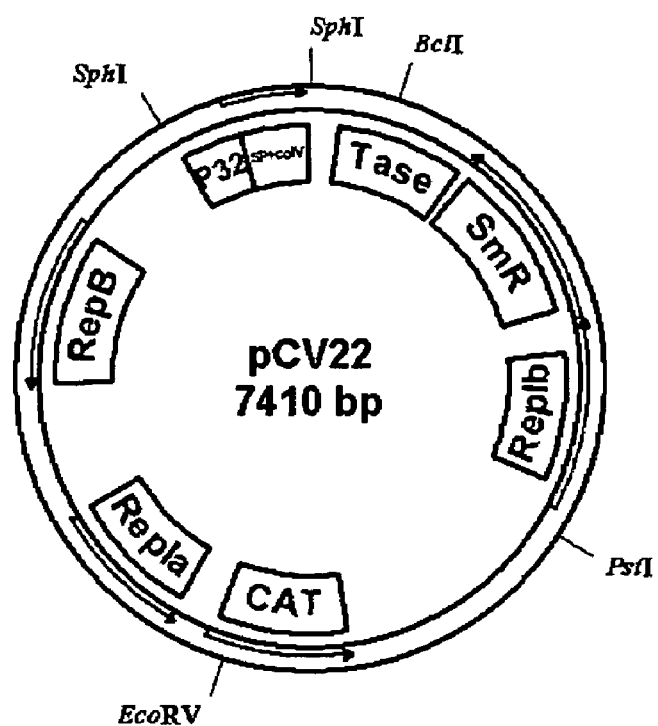
FIG. 2 is a schematic representation of pCV22, and illustrates the replacement of the pCaT mobilization genes (mob) with a colicin V (col V) gene.
Figure 3:
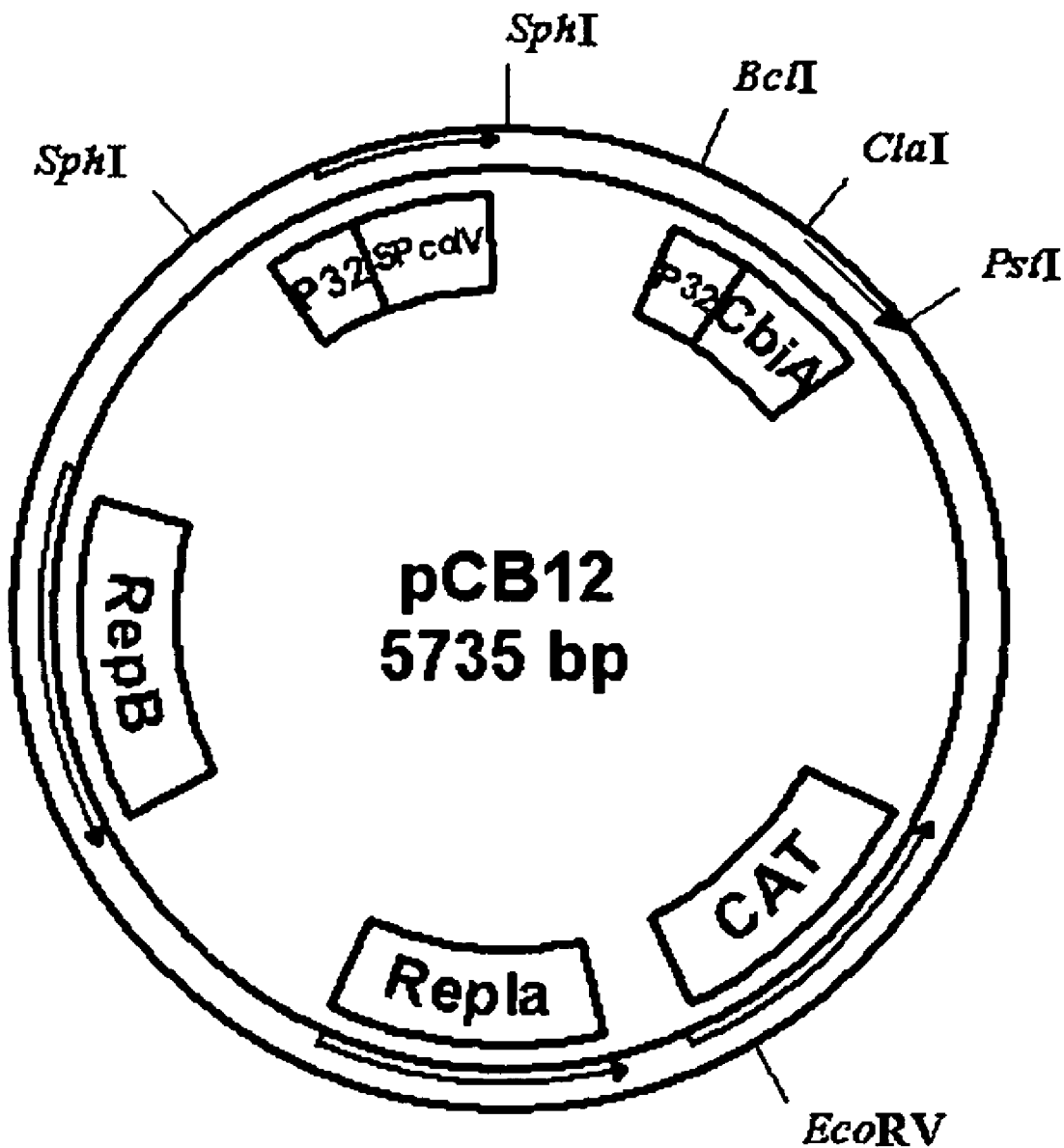
FIG. 3 is a schematic representation of pCB12, and illustrates the replacement of the pCaT streptomycin resistance gene and RepIb gene with a *Carnobacterium* immunity gene (cbiA).

FIG. 1 shows a schematic representation of plasmid pCaT from *Lactobacillus plantarum* caTC2R (Jewell and Collins-Thompson, 1989). The pCaT plasmid was reported to contain the genetic information for chloramphenicol resistance (cat gene). The inventors have fully sequenced and partially characterized the plasmid. The plasmid has been transformed into various *Carnobacterium* spp., *L. plantarum* NC8 and *L. casei* ATCC 393, demonstrating chloramphenicol resistance in these strains (Ahn et al., 1992). The pCaT plasmid contains 8951 base pairs. Several putative genes were located, including genes involved in replication (repB, repIa and repIb), mobilization (mob), antibiotic resistance for chloramphenicol (cat) and streptomycin (str), and a truncated open reading frame that could encode a transposase (Tase) (See FIG. 1). The inventors have used pCaT as a cloning vector for genes related to the production of proteins such as, but not limited to, bacteriocins produced by Gram-positive bacteria.

The P32 promoter was isolated from *Lactococcus lactis* subsp. *lactis* (van der Vossen et al., 1987) and this promoter been used to express colicin V gene in pJKM37 (McCormick et al., 1999). Plasmid pJKM37 contains P32 promoter, divergicin A signal peptide, and colicin V gene (colV). A 28-mer oligonucleotide, (5'-CCC GCATGC TGA ATT CGG TCC TCG GGA T-3') (Seq. I.D. No. 6) containing a SphI restriction site (underlined) that is added to a sequence homologous to the 5' end of the nucleotide sequence containing the P32 promoter in pJKM37 and a 28-mer oligonucleotide, (5'-CCC GCATGC GGT ACC ACT ATT TAT AAA C-3') (Seq. I.D. No. 7) containing a SphI restriction site (underlined) that is added to a sequence homologous to the 3' end of the nucleotide sequence containing the structural gene for colicin V in pJKM37 were used for the PCR reaction with pJKM37 as a template. The PCR product containing P32 promoter and colicin V gene (co/V) fused to divergicin A signal peptide was digested with SphI. The digested PCR product was cloned into pCaT by replacing the 2.1 kb SphI fragment of pCaT containing the mobilization genes. The resulting plasmid, pCV22 (FIG. 2), was transformed into a plasmidless host, *Carnobacterium maltaromaticum* UAL26. These transformed cells inhibited the growth of the colicin V sensitive indicator strain *E. coli* DH5α.

Example 2

Figure 4:
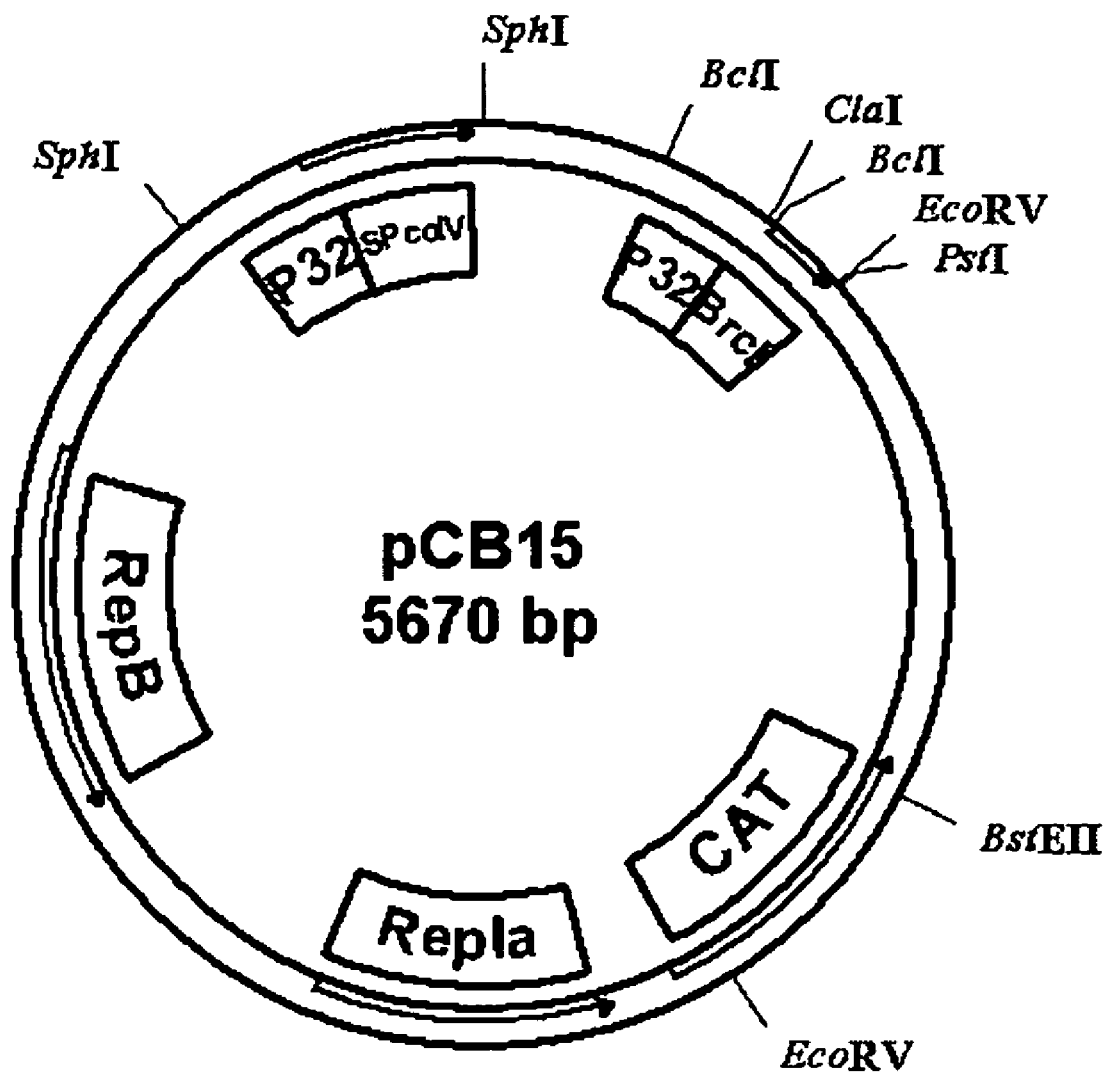
FIG. 4 is a schematic representation of pCB15, and illustrates the replacement in pCB12 of the cbiA gene with a brochocin C immunity gene (brcI). pCB15 includes colicin V (illustrated), and pCB15s includes colicin VM (not illustrated).

Introduction of Bacteriocin Immunity Genes as Selection Markers into Colicin V Producing pCaT Derivatives Transformed into LAB Immunity genes for bacteriocins were introduced into pCV22 as genetic selection markers. Two different functional polynucleotide sequences encoding bacteriocin immunity proteins were selected for this procedure: carnobacteriocin A immunity gene and brochocin-C immunity gene (Franz et al., 2000; McCormick et al., 1998). In plasmid pCF08 the mid-sequence encoding carnobacteriocin A immunity was cloned behind the P32 promoter (functional) (Franz et al., 2000). A 28-mer oligonucleotide (5'-TAT ATGATC AGG TCC TCG GGA TAT GAT A-3') (Seq. I.D. No. 8) containing a BcII restriction site (underlined) was added to a sequence homologous to the 5' end of the nucleotide sequence containing the P32 promoter in pCF08 (Franz et al., 2000) and a 28-mer oligonucleotide (5'-TAT ACTGCAGGG TAC CGT CTA CAG TCT G-3') (Seq. I.D. No. 9) containing a PstI restriction site (underlined) was added to the 3' end of the nucleotide sequence encoding carnobacteriocin A immunity protein in pCF08 were used to amplify the sequence encoding carnobacteriocin A immunity gene under the control of P32. This PCR product was cloned into pCV22 using BcII and PstI restriction sites. The carnobacteriocin A immunity gene of the resulting plasmid, pCB12 (FIG. 3), was subsequently replaced by the immunity gene for the bacteriocin brochocin-C. A 40-mer oligonucleotide (5'-ATA TATCGATAG GM GTA TGA TCAATG GTAAAAACT ATA C-3') (Seq. I.D. No. 10) containing a ClaI restriction site (underlined) was added to the 5' end of the brochocin-C immunity gene in pJKM61 (McCormick et al., 1998) and a 35-mer oligonucleotide (5'-ATA TCTGCAGAT ATC TAG TTA GAG MT ATA ATC CA-3') (Seq. I.D. No. 11) containing a PstI restriction site (underlined) was added to the 3' end of the brochocin-C immunity gene in pJKM61 were used to amplify the immunity gene for brochocin-C. This PCR product was cloned into the ClaI and PstI restriction sites of pCB12, resulting in plasmid pCB15 (FIG. 4). Plasmid pCB15 was transformed into *C. maltaromaticum* UAL26. The transformed strain inhibited the growth of colicin V sensitive indicator organism such as *E. coli* DH5α and showed immunity to brochocin-C [20% heat-treated (100° C. for 5 min) spent supernatant from a culture of *Brochothrix campestris* ATCC 43754 in APT medium].

Example 3

Isolation and Selection of *Lactobacillus reuteri* CB4 for use as a Host to Develop a Targeted Probiotic Organism The gastrointestinal tract (GIT) of two healthy pigs was obtained from a small, provincially inspected meat packing plant at time of slaughter. The GIT was excised, sealed at the anterior and posterior ends and transported to the Animal Science laboratory at the University of Alberta Research Station (Edmonton, Canada). The GIT was flushed with tap water to remove the intestinal contents and segments were excised from the pars esophagea, ileum, jejunum, cecum and colon. The internal surface of the excised segments was scraped with a sterile microscope slide to remove the surface of the epithelial layer.

The scrapings were washed into a dilution bottle, plated onto Difco Lactobacilli MRS agar (MRS) and incubated anaerobically at 37° C. for 18 to 24 hours. A total of 18 morphologically distinct colonies was randomly selected and checked for Gram-positive, catalase negative, rod-shaped characteristics and inoculated into MRS broth for storage. These strains were checked for bacteriological purity and tested for transformability with pCB15. Only *Lactobacillus* spp. that could be transformed were selected for further study. The isolate CB4 was able to be transformed, and was confirmed to be *Lactobacillus reuteri* by 16S rDNA analysis (Willson et al., 1990). *L. reuteri* CB4 was chosen as a strain of interest based on the stability of the transformed plasmid.

Example 4

Production of a Mutated Colicin V Bacteriocin, Colicin VM, in *Lactobacillus reuteri* CB4

Electroporation of pCB15 isolated from *C. maltaromaticum* UAL26 into *L. reuteri* CB4 resulted in a low transformation rate. A *L. reuteri* CB4 transformant was isolated that contained a plasmid denoted pCB15s, that was stable in the host strain and produced a bacteriocin that inhibited growth of colicin V-sensitive indicator organisms such as *E. coli* DH5α. The plasmid pCB15s from *L. reuteri* CB4 was isolated from this transformant and electroporated back into plasmidless *C. maltaromaticum* UAL26. When pCB15s that was re-isolated from these *C. maltaromaticum* UAL26 transformants was electroporated back into *L. reuteri* CB4 a significantly higher transformation frequency was obtained. Nucleotide sequencing of the inserted colicin gene revealed the presence of a mutation in the colicin V gene consisting of a duplication of the nucleotide sequence 5' GTGGCTGGAGGT 3' (Seq. I.D. No. 12). This resulted in duplication of amino acids 29 to 32 of colicin V to give Val-Ala-Gly-Gly-Val-Ala-Gly-Gly (Seq. I.D. No. 13). Hence, the mutated colicin V was named colicin VM. The colicin VM consists of 92 amino acids instead of the 88 amino acids that constitute colicin V (FIG. 5). Both *C. maltaromaticum* UAL26 and *L. reuteri* CB4 transformants containing pCB15s inhibited *E. coli* DH5α indicating that colicin VM retains antibacterial activity against *E. coli*.

Example 5

Use of Genetically Modified Bacteria Producing Recombinant Colicin VM as a Preventative Treatment for Post Weaning Diarrhea (PWD) of Pigs The host strains for use in this technology will be harmless or beneficial (probiotic) microorganisms that are commonly associated with the GI tract of the target animal. Post-weaning diarrhea (PWD) that causes morbidity or mortality of pigs is an example of a GI disease that can be prevented using this technology.

The efficacy of the transformed host strain, *Lactobacillus reuteri* CB4 containing pCB15s, producing colicin VM (coIVM) to target enterotoxigenic *Escherichia coli* (ETEC) that cause post-weaning diarrhea (PWD) in pigs was determined. The organism was tested in an established pig infection model. Efficacy of the preventative treatment is measured by reduction of PWD and normal weight gain of the weanling pigs.

Twenty 17-day-old weaned piglets were divided into two groups of 10 pigs. Group 1 was untreated and Group 2 was treated by administration of approximately $1 \times 10^9$ *L. reuteri* CB4, containing pCB15s in the drinking water from Day 1 to Day 9 of the experiment. On Day 7 both groups were challenged with approximately $5 \times 10^8$ of an ETEC-F4 strain (known to cause PWD), administered by oesophageal tube. In the model the presence of F4 receptor-positive animals (those specifically susceptible to colonization by the ETEC-F4 strain) were selected for separate analysis. Health of the experimental animals was monitored and on Day 10 they pigs were euthanized for necropsy.

The effect of the test organism was measured by analysis of weight gain, the diarrhea score, consistency of the intestinal contents and colonization of the ileum by the challenge strain at the day of necropsy.

RESULTS

From the day of the challenge to the day of necropsy the daily weight gain of Group 2 was higher (continued to grow) than Group 1 (did not grow). In Group 2, the administration of the *L. reuteri* CB4 containing pCB15s, resulted in improved intestinal consistency, particularly in the jejunum and the ileum, and reduced diarrhea scores.

In Group 2 colonization of the ileum with the ETEC-F4 challenge strain was decreased by 1 log compared with Group 1.

The benefit of feeding *L. reuteri* CB4 containing pCB15s to weaned piglets was demonstrated by continued weight gain after the challenge and reduced incidence and degree of diarrhea. In various trials, a significant number of piglets gained weight after the *E. coli* challenge, as compared to control piglets; and a significant number of piglets exhibited reduced and degree of diarrhea in response to the *E. coli* challenge, as compared to the control piglets.

These data were confirmed by results of additional challenge studies.

Example 6

Production of a Mutated Colicin V Bacteriocin, Colicin VM, in a Feed-Grade Vector In these examples a feed-grade vector is a plasmid that lacks or contains a truncated antibiotic resistance genes and uses an alternate selection system, such as a bacteriocin immunity gene, for animal feed applications.

To inactivate the cat gene, a derivative of pCB15, named pCB21 (FIG. 6), was made that has unique EcoRV and BstEII restriction sites in the cat gene. To ensure that the cat gene EcoRV site was unique, an EcoRV restriction site located immediately downstream of the brochocin-C immunity gene of pCB15 was removed by the following procedure: a 40-mer oligonucleotide (5'-ATA TATCGATAG GM GTATGAT-CAATG GTAAAAACT ATA C-3') (Seq. I.D. No. 14) described in Example 2, and a 27-mer oligonucleotide (5'-ATA TCTGCAGTC TAG TTA GAG MT ATA-3') (Seq. I.D. No. 15) containing a PstI restriction site (underlined) fused to the homologous 3' end of the brochocin-C immunity gene in pJKM61 were used to amplify the immunity gene for brochocin-C. This PCR product was cloned into the ClaI and PstI restriction sites of pCB15 to replace the brochocin-C immunity gene that contained the downstream EcoRV restriction enzyme site and transformed into *C. maltaromaticum* UAL26. The resulting plasmid, pCB21 (See FIG. 6), obtained from the transformants was digested by EcoRV and BstEII, filled in by DNA polymerase I and dNTPs, self-ligated, and transformed into *C. maltaromaticum* UAL26. UAL26 transformants were selected by plating on APT plates containing 20% heat-treated (100° C. for 5 min) spent supernatant from a culture of *Brochothrix campestris* ATCC 43754 grown in APT medium. The resulting UAL26 transformants contained plasmid pCB22 (FIG. 7) and were sensitive to chloramphenicol and produced colicin V.

To achieve the production of colicin VM using a feed-grade vector in strains of *lactobacilli* that are unable to produce the native colicin V, the following cloning experiment was done. The 1.5-kb EcoRI-PstI fragment from plasmid pCB15s containing the colicin VM gene was isolated and cloned into the EcoRI-PstI restriction sites of plasmid pCB22. The resulting plasmid, pCB23M (FIG. 8), lost the 1.5-kb EcoRI-PstI fragment that contains the native colicin V gene because it was replaced by the 1.5-kb EcoRI-PstI fragment that contains the colicin VM structural gene. *C. maltaromaticum* UAL26 containing pCB23M inhibited *E. coli* DH5α, was immune to brochocin-C and sensitive to chloramphenicol. Plasmid pCB23M was isolated from *C. maltaromaticum* UAL26 and transferred by electroporation into *L. reuteri* CB4 using 4000 AU/ml of brochocin-C as selection agent. Transformants of CB4 containing pCB23M were sensitive to chloramphenicol, immune to brochocin-C and inhibited growth of the indicator organism *E. coli* DH5α. This result showed that we obtained a strain of *L. reuteri* CB4 that inhibited *E. coli* using a feed-grade plasmid.

Example 7

Use of Plasmid pCB19 as a Cloning Vector in LAB

A cloning vector pCB19 based on pCaT was constructed by introducing a multiple cloning site that can be used to clone DNA fragments of interest. A 4.6-kb SphI-PstI DNA fragment from pCaT that contains the open reading frames that could encode proteins involved in horizontal transfer of plasmids as well as the streptomycin resistance gene was replaced by a polylinker (5'-GCA TGC GAA TTC GAG CTC GGT ACC CGG GGA TCC TCC TGC AG-3') (Seq. I.D. No. 16) that contains multiple cloning sites (FIG. 9). The resulting 4.3-kb plasmid, pCB19 (See FIG. 8), can be selected when transformed into lactic acid bacteria using the chloramphenicol resistance gene (cat). This plasmid has been transformed into lactic acid bacteria such as *C. maltaromaticum* and *L. reuteri*. Other selection markers including, but not limited to, bacteriocin immunity genes can be cloned into the multiple cloning sites of pCB19. The inventors have demonstrated that genes encoding proteins such as bacteriocins can be cloned into the multiple cloning sites of pCB19 resulting in export of the recombinant proteins by the lactic acid bacteria.

Example 8

Screening Promoter from *C. maltoromaticum* Strain

To investigate whether other suitable promoters can be found to express bacteriocin production in LAB, a promoter from the chromosomal DNA of *C. maltaromaticum* LV17 was cloned. Chromosomal DNA was isolated by the inventors from *C. maltaromaticum* LV17, digested completely with the restriction enzyme MboI and cloned into the promoter screening vector pGKV210 (van der Vossen et al., 1985). The ligation mixture was transferred by electroporation into *C. maltaromaticum* UAL26 and transformants were selected on APT agar plates containing 20 μg of chloramphenicol per ml. One such transformant obtained, designated as pGKV210-P15, grew on APT plates with chloramphenicol concentration as high as 45 to 50 μg/ml. The promoter in pGKV210 that was isolated from *C. maltaromaticum* LV17 was labeled P15.

A pair of primers, MP11 forward primer 5' <u>GAATTC</u>GAGCTCGCCCGG 3' (Seq. I.D. No. 17) containing a EcoRI restriction site (underlined) and reverse primer 5' CTGCAGGTCGACTCTAGAG 3' (Seq. I.D. No. 18), were used to amplify the insert containing the P15 promoter from pGKV210-P15. The sequence of the fragment containing the P15 promoter was determined and showed to contain 276 nucleotides (FIG. 10).

Recombinant PCR technique was used to construct plasmids expressing the colicin V gene using the P15 promoter (FIG. 11). The MP11 forward primer (5' GAATTC-GAGCTCGCCCGG 3') (Seq. I.D. No. 19) and a reverse primer A (5' TGTGATACCMGATGCATTCAAC-CATATTTGMG 3') (Seq. I.D. No. 20), which is complemented to the 3'-end of P15 promoter and the DNA encoding the N-terminus of leading peptide of divergicin A, were used to amplify the P15 promoter fragment. Primers B (5' TATG-GTTGAATGCATCTTGGTATCACAAACTAA 3') (Seq. I.D. No. 21) and C (5' CCC <u>GGTACC</u>ACTATTTATAAACAAACATCAC 3') (Seq. I.D. No. 22) (McCormick et al., 1999) were used to amplify the DNA encoding colicin V and the signal peptide of divergicin A using plasmid pCB15 DNA as the template. Primer B is complementary to the 3' end of the P15 promoter fragment and the DNA encoding the N terminus of the signal peptide of divergicin A. Primer C contains a KpnI restriction site (underlined) and is used as the reverse primer for colV. Subsequently, the two PCR products from above were used as templates and the primers MP11 forward and C were used for recombinant PCR to amplify the fragment containing the DNA from both PCR products. The resulting PCR product contains P15 promoter, in front of DNA encoding colicin V fused to the signal peptide of divergicin A.

The above PCR fragment was digested with EcoRI and KpnI restriction enzymes and inserted into the appropriate sites of pCB19, giving plasmid pCB101 (FIG. 12). Plasmid pCB101 was transferred by electroporation into *C. maltaromaticum* UAL26. The strain containing pCB101 inhibited the growth of colicin V indicator strain *E. coli* DH5α.

Example 9

Production of Colicin V using P15 Promoter in *C. maltaromaticum* using a Feed-Grade Vector Primer (5' GTMC <u>TCTAGA</u>AGGMGTATGATCAATGGTA 3') (Seq. I.D. No. 23) containing a XbaI site (underlined) and primer (5' TAT <u>CTGCAG</u>TCTAGTTAGAGMTAT AATCCA 3') (Seq. I.D. No. 24) containing a PstI site (underlined) were used to amplify the brochocin-C immunity gene using pCB15 DNA as the template. The PCR product was inserted into the appropriate sites of pCB101, giving the plasmid pCB103 (FIG. 13). When pCB103 was transformed into *C. maltaromaticum* UAL26, the strain containing the plasmid inhibited the growth of *E. coli* DH5α and was resistant to chloramphenicol.

To construct a feed-grade vector containing colV, plasmid pCB103 was digested with the unique restriction enzyme sites EcoRV and BstEII, which are located within the cat gene, to remove most of the cat gene. The linear fragment was blunted by DNA polymerase 1, self-ligated and transformed into *C. maltaromaticum* UAL26. The resulting feed-grade plasmid pCB104 contains the DNA encoding the signal peptide of divergicin A, fused to colicin V, and brochocin-C immunity, under control of the P15 promoter (FIG. 14). *C. maltaromaticum* UAL26 containing pCB104 was selected on APT agar plates containing 80 AU of brochocin-C per ml. The activity units of brochocin-C using *Carnobacterium divergens* LV13 (Worobo et a. 1995) as the indicator organism were determined as described previously (van Belkum and Stiles, 1995). These strains inhibited the growth of *E. coli* DH5α, and were sensitive to chloramphenicol.

*C. maltaromaticum* UAL26 containing plasmids pCB101, pCB103 and pCB104 all produced a bacteriocin at a similar level that inhibited the growth of *E. coli* DH5α. *C. maltoromaticum* UAL26 containing pCB104 showed resistance to brochocin-C, but sensitivity to chloramphenicol.

Example 10

Use of Promoter P15 to Express the Production of Colicin VM in a Feed-Grade Vector To produce colicin VM using a feed-grade vector in strains of *Lactobacilli* that are unable to produce colicin V, recombinant PCR technique and subcloning were performed. The P15 promoter was amplified by PCR as before using primers MP11 forward and primer A (See FIG. 11) and template pGKV210-P15. colVM gene was amplified by PCR using primers B and C and template pCB23M. Recombinant PCR was used to amplify a DNA fragment containing P15 promoter, the signal peptide of divergicin A, and the colVM. The fragment was amplified using primers MP11 forward and C and the PCR products containing P15 promoter and colVM gene from above as templates.

The fragment obtained cut by EcoRI and KpnI and inserted into plasmid pCB104 appropriate sites by replacing the EcoRI/KpnI fragment in pCB104. The resulting plasmid pCB 110 is feed-grade vector containing P15 promoter and signal peptide of divergicin A fused to colVM (FIG. 15). Alternatively, a feed-grade plasmid, designated as pCB111, was constructed by replace the P32 promoter in pCB23M with P15 promoter. Plasmid pCB111 is similar to pCB23M except it has the P15 promoter instead of P32 promoter. *C. maltatomaticum* UAL26 containing pCB110 or pCB111 shows activity against *E. coli*, sensitivity to chloramphenicol, and resistance to brochocin C. Plasmid pCB110 and pCB111 were transformed into *L. reuteri* CB4. Strain *L. reuteri* CB4 containing pCB110 or pCB111 inhibited the growth of *E. coli*, was sensitive to chloramphenicol and resistant to brochocin C.

REFERENCES CITED

Ahn, C., Collins-Thompson, D., Duncan, C., and Stiles, M. E. 1992. Mobilization and location of the genetic determinant of chloramphenicol resistance from *Lactobacillus plantarum* caTC2R. Plasmid 27: 16-176.

Franz, C. M. A. P., van Belkum, M. J., Worobo, R. W., Vederas, J. C., and Stiles, M. E. 2000. Characterization of the genetic locus responsible for production and immunity of carnobacteriocin A: the immunity gene confers cross-protection to enterocin B. Microbiology 146: 621-631.

Jewell, B., and Collins-Thompson, D. L. 1989. Characterization of chloramphenicol resistance in *Lactobacillus plantarum* caTC2R. Curr. Microbiol. 19: 343-346.

McCormick, J. K., Poon, A., Sailer, M., Gao, Y., Roy, K. L., McMullen, L. M., Vederas, J. C., Stiles, M. E., and van Belkum, M. J. 1998. Genetic characterization and heterologous expression of brochocin-C, an antibotulinal, two-peptide bacteriocin produced by *Brochothrix campestris* ATCC43754. Appl. Environ. Microbiol. 64: 4757-4766.

McCormick, J. K., Klaenhammer, T. R., and Stiles, M. E. 1999. Colicin V can be produced by lactic acid bacteria. Lett. Appl. Microbiol. 29: 37-41.

Sambrook, J., Fritsch, E. F., and Maniatis, T. 1989. Molecular Cloning: A Laboratory Manual, $2^{nd}$ edn. Cold Spring Harbor, N.Y.: Cold Spring Harbor Laboratory Press.

Sanger, F., Nicklen, S., Coulson, A. R. 1977. DNA sequencing with chain-terminating inhibitors. Proc. Natl. Acad. Sci. 74: 5463-5467.

Stiles, M. E., Vederas, J. C., van Belkum, M. J., Worobo, R. W., Worobo, R. J., McCormick, J. K., Greer, G. G., McMullen, L. M., Leisner, J. J., Poon, A., Franz, C. M. A. P. 2002. Bacteriocins, transport and vector system and method of use thereof. U.S. Pat. No. 6,403,082.

van Belkum, M. J., and Stiles, M. E. 1995. Molecular characterization of genes involved in the production of the bacteriocin leucocin A from *Leuconostoc gelidum*. Appl. Environ. Microbiol. 61: 3573-3579.

Van der Vossen, J. M. B. M., Kok, J., and Venema, G. 1985. Construction of cloning, promoter-screening, and terminator-screening shuttle vectors for *Bacillus subtilis* and *Lactococcus lactis* subsp. *lactis*. Appl. Environ. Microbiol. 50: 540-542.

van der Vossen, J. M. B. M., van der Lelie, D., and Venema, G. 1987. Isolation and characterization of *Streptococcus cremoris* Wg2-specific promoters. Appl. Environ. Microbiol. 53: 2452-2457.

Wilson, K. H., Blitchington, R. B., and Greene, R. C. 1990. Amplification of bacterial 16S ribosomal DNA with polymerase chain reaction. J. Clin. Microbiol. 28: 1942-1946.

Worobo, R. W., van Belkum, M. J., Sailer, M., Roy, K. L., Vederas, J. C., and Stiles, M. E. 1995. A signal peptide secretion-dependent bacteriocin from *Carnobacterium divergens*. J. Bacteriol. 177: 3143-3149.

We claim:

1. An expression vector for the secretion of a polypeptide comprising a promoter, a signal sequence operatively associated with the polypeptide, a DNA sequence encoding a mutated colicin V, wherein the mutated colicin V comprises sequence I.D. NO: 1, and a terminator.

2. The expression vector of claim 1 wherein the signal peptide is divergicin A.

3. A composition comprising the expression vector of claim 1.

4. A lactic acid bacterium comprising the expression vector of claim 1.

* * * * *